United States Patent
Kawaguchi et al.

(10) Patent No.: US 10,023,583 B2
(45) Date of Patent: Jul. 17, 2018

(54) BICYCLIC PYRIDINE COMPOUND

(71) Applicants: Astellas Pharma Inc., Chuo-ku (JP);
KOTOBUKI PHARMACEUTICAL CO., LTD., Hanishina-gun (JP)

(72) Inventors: Kenichi Kawaguchi, Tokyo (JP);
Akihiro Ishihata, Tokyo (JP); Akira Kanai, Tokyo (JP); Yusuke Inagaki, Tokyo (JP); Masashi Hiramoto, Tokyo (JP); Kentaro Enjo, Ibaraki (JP);
Hajime Takamatsu, Tokyo (JP)

(73) Assignees: Astellas Pharma Inc., Chuo-ku (JP);
KOTOBUKI PHARMACEUTICAL CO., LTD., Hanishina-gun (JP)

( * ) Notice: Subject to any disclaimer, the term of this patent is extended or adjusted under 35 U.S.C. 154(b) by 0 days.

(21) Appl. No.: 15/551,222

(22) PCT Filed: Nov. 27, 2015

(86) PCT No.: PCT/JP2015/083345
§ 371 (c)(1),
(2) Date: Aug. 15, 2017

(87) PCT Pub. No.: WO2016/143200
PCT Pub. Date: Sep. 15, 2016

(65) Prior Publication Data
US 2018/0022755 A1  Jan. 25, 2018

(30) Foreign Application Priority Data
Mar. 9, 2015  (JP) .................... 2015-046121

(51) Int. Cl.
C07D 213/02 (2006.01)
C07D 407/04 (2006.01)
A61K 31/5365 (2006.01)
C07D 491/048 (2006.01)
C07D 495/04 (2006.01)

(52) U.S. Cl.
CPC ....... *C07D 491/048* (2013.01); *C07D 495/04* (2013.01)

(58) Field of Classification Search
CPC . C07D 213/02; C07D 407/04; A61K 31/5365
USPC ......................... 546/255; 514/302
See application file for complete search history.

(56) References Cited

U.S. PATENT DOCUMENTS

| 9,067,948 B2 | 6/2015 | Harriman et al. |
| 2011/0212973 A1 | 9/2011 | Ishii et al. |
| 2016/0002218 A1 | 1/2016 | Takahashi et al. |

FOREIGN PATENT DOCUMENTS

| WO | WO 2010/053120 A1 | 5/2010 |
| WO | WO 2011/136307 A1 | 11/2011 |
| WO | WO 2014/011906 A2 | 1/2014 |
| WO | WO 2014/133056 A1 | 9/2014 |
| WO | 2015182686 | * 3/2015 |
| WO | WO 2015/182686 A1 | 12/2015 |

OTHER PUBLICATIONS

International Search Report dated Jan. 12, 2016 in PCT/JP2015/083345.
Masakazu Ishii, et al., "Oxytocin Hypersensitivity in Pregnant P-LAP Deficient Mice" Life Sciences, vol. 84, 2009, pp. 668-672.
Hanna Andersson, et al., "Potent Macrocydic Inhibitors of Insurin-Regulated Aminopeptidase (IRAP) by Olefin Ring-Closing Metathesis" Journal of Medicinal Chemistry, vol. 54, 2011, pp. 3779-3792.
Examination Report dated Feb. 22, 2018 issued in corresponding GC patent application No. 2015-30478.

* cited by examiner

*Primary Examiner* — Niloofar Rahmani
(74) *Attorney, Agent, or Firm* — Oblon, McClelland, Maier & Neustadt, L.L.P.

(57) ABSTRACT

The problem to be solved by the present invention is to provide a compound suitable for a pharmaceutical composition, specifically a pharmaceutically composition for treating nocturia.
The inventors have assumed that inhibition of nocturnal activity of placental leucine aminopeptidase (P-LAP), i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP. As a result, the inventors have found that (2R)-3-amino-2-(bi-cyclic pyridylmethyl)-2-hydroxypropanoic acid derivatives have excellent P-LAP inhibitory activity. The inventors have evaluated antidiuretic effects in water-loaded rats and have found that the compounds increase endogenous AVP levels by inhibiting P-LAP and consequently reduce urine production. The present invention therefore provides compounds expected to be used as an agent for treating nocturia based on P-LAP inhibition.

17 Claims, No Drawings

BICYCLIC PYRIDINE COMPOUND

TECHNICAL FIELD

The present invention relates to a bi-cyclic pyridine compound or a salt thereof which is useful as a pharmaceutical, specifically a pharmaceutical for treating nocturia, and to a pharmaceutical containing such a compound as an active ingredient.

BACKGROUND ART

Nocturia is a lower urinary tract symptom defined as "the complaint that the individual has to wake at night one or more times to void" (Neurourol Urodyn 2002; 21: 167-178). Nocturia prevalence increases with age (J Urol 2010; 184: 440-446), and major patients with nocturia are older adults. It impairs quality of life (QOL) in that it disrupts sleep (Eur Urol 2010; 57: 488-498) and increases risk of fracture. Causes of nocturia are global polyuria, nocturnal polyuria, reduced bladder capacity, and sleep disorders, but in many patients nocturia is considered to be multifactorial (Eur Urol 2012; 62: 877-890). Nocturnal polyuria is defined as nocturnal urine volume greater than 33% of the 24-hour urine volume and is present in about 80% of the patients with nocturia (J Urol 2011; 186: 1358-1363).

Arginine-vasopressin (hereinafter, abbreviated as AVP) is an antidiuretic hormone that is a peptide consisting of nine amino acids, and is biosynthesized and secreted in the hypothalamic-pituitary gland axis. AVP receptors are classified into three subtypes: V1a, V1b, and V2. Known major pharmacological actions of AVP in the periphery are vasoconstriction through the V1a receptor, and antidiuresis through the V2 receptor. AVP acts on the renal tubules to promote renal water reabsorption, decreasing the urine volume. For this reason, decreased nocturnal AVP secretion with age is assumed to be a cause of increased nocturnal urine volume (J Int Med 1991; 229: 131-134, BJU Int 2004; 94: 571-575).

Stimulation of the V2 receptor is expected to improve nocturia. Desmopressin (hereinafter, abbreviated as dDAVP) is a selective V2 receptor agonist used for treating patients with nocturia, and is reported to decrease nocturnal urine volume and the number of nocturnal voids, resulting in an increased duration of initial undisturbed sleep (J Urol 2013; 190: 958-964, and J Urol 2013; 190: 965-972). Unfortunately, V2 receptor agonists theoretically induce fluid retention and increase risks of hyponatremia. It is reported that V2 receptor agonists should be administered with caution and monitoring of serum sodium level to older adults who are the majority of patients with nocturia (Neurourol Urodyn 2004; 23: 302-305).

Placental leucine aminopeptidase (hereinafter, abbreviated as P-LAP) is an enzyme that degrades L-leucine-β-naphthylamide, oxytocin and AVP (Arch Biochem Biophys 1992; 292: 388-392), and was cloned as an aminopeptidase by Rogi et al. in year 1996 (J Biol Chem 1996; 271: 56-61). The insulin-regulated aminopeptidase (hereinafter, abbreviated as IRAP) cloned by Keller et al. from rat epididymal fat pads has homology of 87% to human P-LAP. The IRAP is subsequently suggested to be an aminopeptidase that cleaves AVP and reported to be a rat homolog of human P-LAP (J Biol Chem 1995; 270: 23612-23618, Am J Physiol Endocrinol Metab 2007; 293: E1092-E1102). Angiotensin IV ($AT_4$) receptor isolated from bovine adrenal is also suggested to be an IRAP as a result of biochemical and pharmacological studies (J Biol Chem 2001; 276: 48623-48626).

Experiments using P-LAP knockout mice indicate that administration of AVP in wild type mice and P-LAP knockout mice results in much reduction of 24-h urine volume in P-LAP knockout mice, although no significant difference is observed in the 24-h urine volume between the wild type and P-LAP knockout mice. It suggests the possible involvement of P-LAP in regulation of the urine volume through degradation of AVP (NPL 1).

Compounds represented by Formula (A) below are reported to be IRAP inhibitors useful as a therapeutic agent for dementia and diabetes, and the like (PTLs 1 and 2).

[Chemical Formula 1]

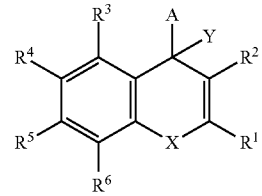

(A)

wherein X is O, NR' or S, and other symbols are defined as in PTLs 1 and 2.

Tripeptide analogs of $AT_4$ with 13- to 14-membered ring structure exhibits excellent IRAP inhibitory activity (NPL 2).

However, no antidiuretic agent or therapeutic agents for nocturia based on a mechanism mediated by P-LAP (or IRAP) has been reported.

Under such circumstances, there exists need for a safe antidiuretic agent that is suitable for treating nocturia.

CITATION LIST

Patent Literature

[PTL 1] WO 2006/026832
[PTL 2] WO 2009/065169

Non Patent Literature

[NPL 1] Life Sciences 84 (2009) 668-672
[NPL 2] J Med Chem 2011; 54; 3779-3792

SUMMARY OF INVENTION

Technical Problem

The present invention provides a compound useful as an active ingredient of a pharmaceutical composition, specifically a pharmaceutical composition for treating nocturia.

Means for Solving Problem

The inventors have assumed that inhibition of nocturnal activity of P-LAP, i.e. aminopeptidase that cleaves AVP, would maintain and/or increase an endogenous AVP level to enhance the antidiuretic effect, which would contribute to a decreased number of nocturnal voids, and have extensively studied compounds which inhibit P-LAP (including rat IRAP, a homolog of human P-LAP).

As a result, the inventors have found that a compound represented by Formula (I) below has excellent P-LAP inhibitory activity. The inventors have evaluated antidiuretic effects in water-loaded rats and have found that the compound represented by Formula (I) increases endogenous AVP levels by inhibiting P-LAP and consequently reduces urine production. Based on such findings, the inventors have accomplished the present invention.

The present invention relates to a compound represented by Formula (I) or a salt thereof, and a pharmaceutical composition comprising the compound represented by Formula (I) or a salt thereof and an excipient:

[Chemical Formula 2]

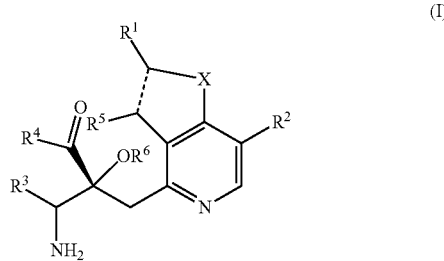

(I)

wherein, X is O or S;
a dotted line is a single bond or a double bond;
$R^1$ is lower alkyl which optionally has one to four substituents selected from the Group $G^1$, cycloalkyl which optionally has one to five substituents selected from the Group $G^2$, or -lower alkylene-(cycloalkyl which optionally has one to five substituents selected from the Group $G^2$);
$R^2$ and $R^5$ are the same or different from each other, and are H, lower alkyl or cycloalkyl;
$R^3$ is -lower alkylene-$X^3$-lower alkyl, -lower alkylene-$X^3$-lower alkylene-(cycloalkyl which optionally has one to five substituents selected from the Group $G^2$), -lower alkylene-(cycloalkyl which optionally has one to five substituents selected from the Group $G^2$), or -lower alkylene-$X^3$-(cycloalkyl which optionally has one to five substituents selected from the Group $G^2$);
$X^3$ is O or $S(O)_n$, wherein n is 0, 1, or 2;
$R^4$ is OH, $NH_2$, or —O-lower alkyl and $R^6$ is H; or $R^4$ and $R^6$ are linked to each other to form, together with —C(=O)—C—O— to which they are attached, 2,2-di(lower alkyl)-4-oxo-1,3-dioxolane-5,5-diyl;
the Group $G^1$ consists of halogen, OH, —O-lower alkyl, —S-lower alkyl, and —O-(lower halogenoalkyl); and
the Group $G^2$ consists of lower alkyl, halogen, lower halogenoalkyl, OH, —O-lower alkyl, —S-lower alkyl, and —O-lower halogenoalkyl.

As used herein, if a symbol used in a chemical formula is also used in other chemical formula, identical symbols have the same definition, unless otherwise specified.

The present invention also relates to a pharmaceutical composition comprising the compound represented by Formula (I) or a salt thereof. The pharmaceutical composition encompasses an agent for treating nocturia. The present invention also relates to a pharmaceutical composition for treating nocturia comprising the compound represented by Formula (I) or a salt thereof and an excipient.

The present invention also relates to use of the compound represented by Formula (I) or a salt thereof for production of a pharmaceutical composition for treating nocturia, use of the compound represented by Formula (I) or a salt thereof for treating nocturia, the compound represented by Formula (I) or a salt thereof for treating nocturia, and a method of treating nocturia comprising administering to a subject an effective amount of the compound represented by Formula (I) or a salt thereof. As used herein, "subject" is a human or non-human animal in need of a therapeutic treatment, and in one embodiment, a human in need of the therapeutic treatment.

Effects of Invention

The compound represented by Formula (I) or a salt thereof has inhibitory activity against P-LAP, i.e. the AVP-degrading enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

DESCRIPTION OF EMBODIMENTS

Hereinafter, the present invention will be described in detail.

In the present specification, the "lower alkyl" is a straight or branched alkyl having one to ten carbon atoms (hereinafter, abbreviated as $C_{1-10}$); specifically, methyl, ethyl, n-propyl, isopropyl, n-butyl, isobutyl, sec-butyl, tert-butyl, n-pentyl, isopentyl, 3-ethylpentyl, 4-ethylhexyl, 4-ethylheptyl, n-hexyl, isohexyl, isoheptyl, isooctyl, hexan-2-yl, 4-methylpentan-2-yl, 2,2-dimethylpropyl, 3,3-dimethylpentyl or 3,3-dimethylbutyl. In one embodiment, the "lower alkyl" is a straight or branched $C_{1-6}$ alkyl, in one embodiment, a $C_{1-4}$ alkyl; in one embodiment, the "lower alkyl" is methyl, ethyl, n-propyl or isopropyl; in one embodiment, methyl or ethyl.

The "lower alkyl" in the definition of $R^1$ is, in one embodiment, methyl, ethyl, propyl, n-butyl, isobutyl, n-pentyl, isopentyl, n-hexyl, isohexyl, 4-methylhexyl, n-heptyl or isoheptyl; in one embodiment, ethyl, n-butyl, n-pentyl or isopentyl.

The "lower alkyl" in the "-lower alkylene-$X^3$-lower alkyl" in the definition of $R^3$ is, in one embodiment, methyl, ethyl, n-propyl, isopropyl, n-butyl, isobutyl, sec-butyl, tert-butyl, n-pentyl, isopentyl, isohexyl, isoheptyl, isooctyl, 3-ethylpentyl, 4-ethylhexyl, 4-ethylheptyl, n-hexyl, hexan-2-yl, 4-methylpentan-2-yl, 2,2-dimethylpropyl, 3,3-dimethylpentyl or 3,3-dimethylbutyl; in one embodiment, a $C_{1-4}$ alkyl. In one embodiment, methyl, ethyl, n-propyl, isopropyl or isobutyl. In one embodiment, methyl or ethyl.

The "lower alkylene" is a $C_{1-10}$ straight or branched alkylene; specifically, methylene, ethylene, trimethylene, tetramethylene, pentamethylene, hexamethylene, heptamethylene, octamethylene, methylmethylene, propylene, 2-methyltrimethylene, ethylethylene, 1,2-dimethylethylene or 1,1,2,2-tetramethyl ethylene. In one embodiment, a $C_{1-6}$ alkylene; in one embodiment, a $C_{1-4}$ alkylene; in one embodiment, methylene, ethylene, trimethylene, tetramethylene or 2-methyltrimethylene; in one embodiment, methylene, ethylene or trimethylene. The "lower alkylene" is, in one embodiment, methylene or ethylene; in one embodiment, methylene.

The "halogen" is F, Cl, Br or I; and in one embodiment, Cl.

The "lower halogenoalkyl" is a straight or branched $C_{1-10}$ alkyl substituted by one or more halogens. The "lower halogenoalkyl" is, in one embodiment, a $C_{1-6}$ alkyl substituted by one to five halogens; in one embodiment, trifluoromethyl, trifluoroethyl, trifluoropropyl, 2-fluoro-2-methylpropyl, difluoromethyl, fluoromethyl or chloromethyl; and in one embodiment, trifluoromethyl.

The "cycloalkyl" is a $C_{3-12}$ saturated hydrocarbon ring group which is optionally cross-linked and optionally forms a spiro ring. The "$C_{3-12}$ cycloalkyl" is, specifically, cyclopropyl, cyclobutyl, cyclopentyl, cyclohexyl, cycloheptyl, cyclooctyl, bicyclo[2,2,1]heptyl, bicyclo[3,1,0]hexyl, bicyclo[3,1,1]heptyl, adamantyl, spiro[2,5]octyl, spiro[3,5]nonyl or spiro[4,5]decyl. In one embodiment, a "$C_{3-10}$ cycloalkyl"; in one embodiment, a "$C_{3-8}$ cycloalkyl"; in one embodiment, a "$C_{3-6}$ cycloalkyl." The "cycloalkyl" is, in one embodiment, cyclopropyl, cyclobutyl, cyclopentyl, cyclohexyl or cycloheptyl; in one embodiment, cyclopropyl, cyclobutyl or cyclopentyl; in one embodiment, cyclopropyl. In one embodiment, cyclopropyl or cyclobutyl.

The compound represented by Formula (I) includes the compounds having any one of 4 kinds of ring represented by the following formulae. Formula (I-1) is a compound having a furo[3,2-c]pyridine ring wherein X is O, a dotted line is a double bond; Formula (I-2) is a compound having a dihydrofuro[3,2-c]pyridine ring wherein X is O, a dotted line is a single bond; Formula (I-3) is a compound having a thieno[3,2-c]pyridine ring wherein X is S, a dotted line is a double bond; and Formula (I-4) is a compound having a dihydrothieno[3,2-c]pyridine ring wherein X is S, a dotted line is a single bond. In one embodiment, the compound represented by Formula (I) or a salt thereof is the compound of Formula (I-1), Formula (I-2) or Formula (I-3), or a salt thereof; in one embodiment, the compound of Formula (I-1) or a salt thereof.

[Chemical Formula 3]

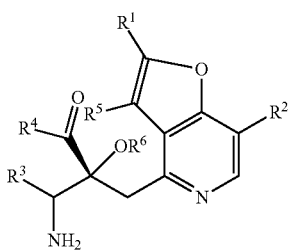

(I-1)

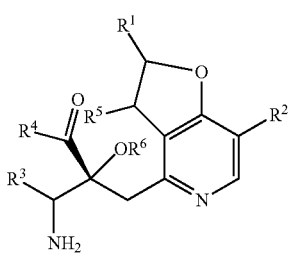

(I-2)

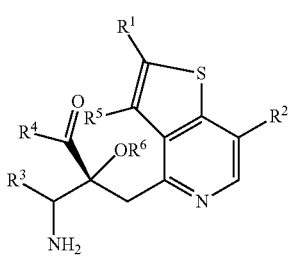

(I-3)

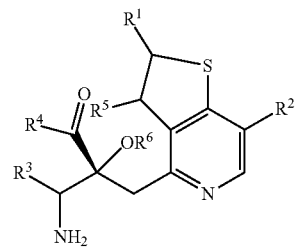

(I-4)

The phrase "$R^4$ and $R^6$ are linked to each other to form, together with —C(=O)—C—O— to which they are attached, 2,2-di(lower alkyl)-4-oxo-1,3-dioxolane-5,5-diyl" means that the compound represented by Formula (I) includes compounds represented by the following Formula (I-A).

[Chemical Formula 4]

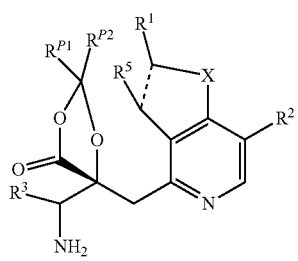

(I-A)

wherein, $R^{P1}$ and $R^{P2}$ are the same or different from each other, and are a lower alkyl, in one embodiment, both $R^{P1}$ and $R^{P2}$ represent methyl.

In the present specification, the "optionally has substituents" means that the specified group is unsubstituted or has substituents; specifically, the "optionally has one to five substituents" means that the specified group is unsubstituted or has one to five substituents. If the specified group has a plurality of substituents, the substituents may be the same or different from each other.

The compound represented by Formula (I) has at least two asymmetric carbon atoms. One asymmetric carbon atom attached to —C(O)$R^4$ (position 2) has (R) configuration, and neighboring carbon atom attached to —NH$_2$ (position 3) may have either (R) or (S) configuration, and the compound represented by Formula (I) includes (R) or (S) isomer on position 3, and a mixture thereof. In one embodiment, the compound represented by Formula (I) is a compound represented by Formula (I') or a salt thereof:

[Chemical Formula 5]

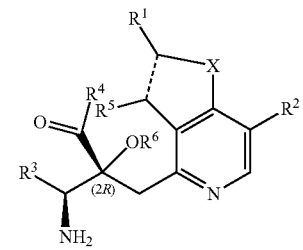

(I')

wherein, (2R) indicates that the carbon atom at position 2 has (R) configuration.

The compound represented by Formula (I) may have tautomers and geometric isomers, depending on the type of substituent groups. The compound represented by Formula (I) also includes separate tautomers and geometric isomers, and mixtures thereof.

The compound represented by Formula (I) may also have stereoisomers based on other asymmetric carbon atom than those described above or the sulfoxide moiety, depending on the type of substituent groups. The compound represented by Formula (I) also includes separate stereoisomers and mixtures thereof.

The present invention also encompasses a pharmaceutically acceptable prodrug of the compound represented by Formula (I). A pharmaceutically acceptable prodrug is a compound having a group which can be converted into an amino group, a hydroxyl group, or a carboxyl group as a result of solvolysis or under physiological conditions. Examples of a group forming a prodrug are described in Prog. Med., 5, 2157-2161 (1985), "Iyakuhin no Kaihatsu (Pharmaceutical Research and Development)" (Hirokawa-Shoten Ltd.), 1990, Vol. 7, "Bunshi Sekkei (Drug Molecular Design)", pp. 163-198, or "Prodrugs and targeted delivery" (Wiley-VCH 2011) Methods and principles in medicinal chemistry, volume 47.

The salt of the compound represented by Formula (I) is a pharmaceutically acceptable salt of the compound represented by Formula (I). The compound represented by Formula (I) may form an acid addition salt or a salt with a base, depending on the type of substituent groups. Specific examples of the salt include acid addition salts with inorganic acids such as hydrochloric acid, hydrobromic acid, hydroiodic acid, sulfuric acid, nitric acid, and phosphoric acid; acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with metal cations such as sodium, potassium, magnesium, calcium, and aluminum; salts with organic bases such as methylamine, ethylamine, and ethanolamine; salts with various amino acids and amino acid derivatives such as acetylleucine, lysine, and ornithine; and ammonium salts.

The present invention also encompasses various hydrates, solvates, and crystalline polymorphs of the compound represented by Formula (I) and a salt thereof. The present invention also encompasses various compounds labeled with a radioactive or nonradioactive isotope.

Some embodiments of the compound represented by Formula (I) are shown below.

(1-1) The compound or a salt thereof, in which X is O or S, and a dotted line is a single bond or a double bond.

(1-2) The compound or a salt thereof, in which X is O, and a dotted line is a single bond or a double bond; or X is S, and a dotted line is a double bond.

(1-3) The compound or a salt thereof, in which X is O, and a dotted line is a single bond or a double bond.

(1-4) The compound or a salt thereof, in which X is O, and a dotted line is a double bond.

(1-5) The compound or a salt thereof, in which X is O, and a dotted line is a single bond.

(1-6) The compound or a salt thereof, in which X is S, and a dotted line is a double bond.

(2-1) The compound or a salt thereof, in which $R^1$ is lower alkyl which optionally has one to four substituents selected from the Group $G^1$, cycloalkyl which optionally has one to five substituents selected from the Group $G^2$, or -lower alkylene-(cycloalkyl which optionally has one to five substituents selected from the Group $G^2$).

(2-2) The compound or a salt thereof, in which $R^1$ is lower alkyl which optionally has one to four substituents selected from the group consisting of halogen, OH, and —O-lower alkyl; cycloalkyl which is optionally substituted by one to two lower alkyls; or -lower alkylene-(cycloalkyl which is optionally substituted by one to two lower alkyls).

(2-3) The compound or a salt thereof, in which $R^1$ is lower alkyl which optionally has one to four substituents selected from the group consisting of halogen and OH; cycloalkyl; or -lower alkylene-cycloalkyl.

(2-4) The compound or a salt thereof, in which $R^1$ is lower alkyl, cycloalkyl, or -lower alkylene-cycloalkyl.

(2-5) The compound or a salt thereof, in which $R^1$ is lower alkyl or -lower alkylene-cycloalkyl.

(2-6) The compound or a salt thereof, in which $R^1$ is n-butyl, isopentyl, cyclopentyl or 2-cyclopropylethyl.

(2-7) The compound or a salt thereof, in which $R^1$ is n-butyl or 2-cyclopropylethyl.

(2-8) The compound or a salt thereof, in which $R^1$ is n-butyl.

(2-9) The compound or a salt thereof, in which $R^1$ is 2-cyclopropylethyl.

(3-1) The compound or a salt thereof, in which $R^3$ is -lower alkylene-$X^3$-lower alkyl, -lower alkylene-$X^3$-lower alkylene-(cycloalkyl which optionally has one to five substituents selected from the Group $G^2$), -lower alkylene-(cycloalkyl which optionally has one to five substituents selected from the Group $G^2$), or -lower alkylene-$X^3$-(cycloalkyl which optionally has one to five substituents selected from the Group $G^2$); $X^3$ is O or $S(O)_n$, wherein n is 0, 1 or 2.

(3-2) The compound or a salt thereof according to the embodiment (3-1), in which $R^3$ is -lower alkylene-$X^3$-lower alkyl, -lower alkylene-$X^3$-lower alkylene-(cycloalkyl which is optionally substituted by one to two lower alkyls), -lower alkylene-(cycloalkyl which is optionally substituted by one to two lower alkyls), or -lower alkylene-$X^3$-(cycloalkyl which is optionally substituted by one to two lower alkyls).

(3-3) The compound or a salt thereof, in which $R^3$ is -lower alkylene-$S(O)_n$-lower alkyl, -lower alkylene-O-lower alkylene-cycloalkyl, -lower alkylene-S-lower alkylene-cycloalkyl, -lower alkylene-cycloalkyl, or -lower alkylene-S-cycloalkyl.

(3-4) The compound or a salt thereof, in which $R^3$ is -lower alkylene-S-lower alkyl, -lower alkylene-O-lower alkylene-cycloalkyl, -lower alkylene-S-lower alkylene-cycloalkyl, -lower alkylene-cycloalkyl, or -lower alkylene-S-cycloalkyl.

(3-5) The compound or a salt thereof, in which $R^3$ is -lower alkylene-S-lower alkyl, or -lower alkylene-cycloalkyl.

(3-6) The compound or a salt thereof, in which $R^3$ is -lower alkylene-S-lower alkyl.

(3-7) The compound or a salt thereof, in which $R^3$ is -lower alkylene-cycloalkyl.

(3-8) The compound or a salt thereof, in which $R^3$ is methylthiomethyl, ethylthiomethyl, n-propylthiomethyl, isopropylthiomethyl, isobutylthiomethyl, cyclopropylmethylthiomethyl, cyclopropylmethyloxymethyl, 2-cyclopropylethyl, 3-cyclopropylpropyl, 2-cyclobutylethyl or cyclobutylthiomethyl.

(3-9) The compound or a salt thereof, in which $R^3$ is methylthiomethyl, ethylthiomethyl or 2-cyclopropylethyl.

(4-1) The compound or a salt thereof, in which $R^2$ and $R^5$ are the same or different from each other, and are H, lower alkyl or cycloalkyl.

(4-2) The compound or a salt thereof, in which $R^2$ and $R^5$ are the same or different from each other, and are H or lower alkyl.

(4-3) The compound or a salt thereof, in which $R^2$ is H or lower alkyl, and $R^5$ is H.

(4-4) The compound or a salt thereof, in which $R^2$ and $R^5$ are both H.

(4-5) The compound or a salt thereof, in which $R^2$ is lower alkyl, and $R^5$ is H.

(4-6) The compound or a salt thereof, in which $R^2$ is methyl, and $R^5$ is H.

(5-1) The compound or a salt thereof, in which $R^4$ is OH, $NH_2$ or —O-lower alkyl and $R^6$ is H; or $R^4$ and $R^6$ are linked to each other to form, together with —C(=O)—C—O— to which they are attached, 2,2-di(lower alkyl)-4-oxo-1,3-dioxolane-5,5-diyl.

(5-2) The compound or a salt thereof, in which $R^4$ is OH, $NH_2$ or —O-lower alkyl and $R^6$ is H.

(5-3) The compound or a salt thereof, in which $R^4$ is OH or —O-lower alkyl and $R^6$ is H.

(5-4) The compound or a salt thereof, in which $R^4$ is OH and $R^6$ is H.

(6) The compound or a salt thereof, according to a combination of any one of the embodiments (1-1) to (1-6), any one of the embodiments (2-1) to (2-9), any one of the embodiments (3-1) to (3-9), any one of the embodiments (4-1) to (4-6), and any one of the embodiments (5-1) to (5-4). Specifically the following combinations are included, but the compound or a salt thereof is not limited thereto.

(6-1) The compound or a salt thereof, according to a combination of the embodiments (1-1), (2-1), (3-1), (4-1), and (5-2).

(6-2) The compound or a salt thereof, according to a combination of the embodiments (1-2), (2-1), (3-1), (4-1), and (5-2).

(6-3) The compound or a salt thereof, according to a combination of the embodiments (1-4), (2-1), (3-1), (4-1), and (5-2).

(6-4) The compound or a salt thereof, according to a combination of the embodiments (1-5), (2-1), (3-1), (4-1), and (5-2).

(6-5) The compound or a salt thereof, according to a combination of the embodiments (1-6), (2-1), (3-1), (4-1), and (5-2).

(6-6) The compound or a salt thereof, according to a combination of the embodiments (1-2), (2-2), (3-2), (4-2), and (5-2).

(6-7) The compound or a salt thereof, according to a combination of the embodiments (1-2), (2-3), (3-3), (4-2), and (5-2).

(6-8) The compound or a salt thereof, according to a combination of the embodiments (1-2), (2-4), (3-4), (4-3), and (5-4).

(6-9) The compound or a salt thereof, according to a combination of the embodiments (1-4), (2-5), (3-5), (4-3), and (5-4).

(6-10) The compound or a salt thereof, according to a combination of the embodiments (1-4), (2-6), (3-6), (4-5), and (5-4).

(6-11) The compound or a salt thereof, according to a combination of the embodiments (1-4), (2-7), (3-6), (4-4), and (5-4).

(6-12) The compound or a salt thereof, according to a combination of the embodiments (1-4), (2-7), (3-7), (4-4), and (5-4).

(6-13) The compound or a salt thereof, according to a combination of the embodiments (1-2), (2-8), (3-8), (4-3), and (5-4).

(6-14) The compound or a salt thereof, according to a combination of the embodiments (1-2), (2-9), (3-9), (4-3), and (5-4).

The compound represented by Formula (I) is, in one embodiment, a compound represented by Formula (I') according to any one of the embodiments (6) or (6-1) to (6-14).

The compound represented by Formula (I) or a salt thereof is, in one embodiment, a compound selected from the group consisting of the following compounds, or a salt thereof.

(2R,3R)-3-Amino-2-{[2-(2-cyclopropylethyl)furo[3,2-c]pyridin-4-yl]methyl}-4-(ethyl sulfanyl)-2-hydroxybutanoic acid, (2R,3S)-3-amino-5-cyclopropyl-2-{[2-(2-cyclopropylethyl)furo[3,2-c]pyridin-4-yl]methyl}-2-hydroxypentanoic acid, (2R,3R)-3-amino-2-{[2-(2-cyclopropylethyl)furo[3,2-c]pyridin-4-yl]methyl}-2-hydroxy-4-(methylsulfanyl)butanoic acid, and (2R,3R)-3-amino-2-[(2-butyl-7-methylfuro[3,2-c]pyridin-4-yl)methyl]-2-hydroxy-4-(methylsulfanyl)butanoic acid.

(Preparation Methods)

The compound represented by the formula (I) or a salt thereof can be prepared using the characteristics based on the basic structure or the type of substituents and by applying various known synthesis methods. During the preparation, replacement of the functional group with a suitable protective group (a group that can be easily converted into the functional group) at the stage from starting material to an intermediate may be effective depending on the type of functional groups in the production technology in some cases. Such a protective group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

Hereinbelow, the representative preparation methods for the compound represented by the formula (I) will be described. Each of the production processes may also be carried out with reference to the References appended in the present description. Further, the preparation methods of the present invention are not limited to the examples as shown below.

(Production Process 1)

[Chemical Formula 6]

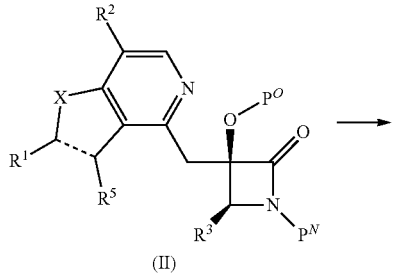

(II)

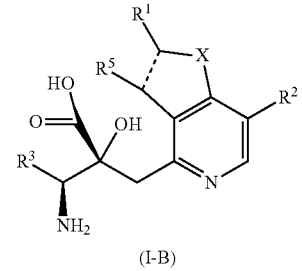

(I-B)

In the formula, $P^O$ represents a protective group for a hydroxyl group, and $P^N$ represents a protective group for an amino group.

The compound (I-B) in which $R^4$ is OH in Formula (I) can be prepared by ring-opening and deprotection of the compound (II).

le;3qIn this reaction, the compound (II) and a hydrolytic reagent in equivalent amounts, or either thereof in an excess amount, are used, and the mixture is stirred for usually 0.1 hour to five days in a solvent which is inert to the reaction under from cooling to heating with reflux. Examples of the solvent used herein are not particularly limited, but include alcohols such as methanol, ethanol and n-propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such solvent(s) and water is preferably used for the reaction. Examples of the hydrolytic reagent used herein are not particularly limited, but include bases such as aqueous sodium hydroxide solution and aqueous potassium hydroxide solution; and acids such as hydrogen chloride and trifluoroacetic acid. In some cases, it is preferred to treat the compound (II) with a base and then with an acid, or to treat it with an acid and then with a base.

Examples of $P^O$, the protective group for a hydroxyl group, include methoxymethyl, benzyloxymethyl and the like. Examples of $P^N$, the protective group for an amino group, include methoxymethyl, benzyloxymethyl and the like.

(Production Process 2)

[Chemical Formula 7]

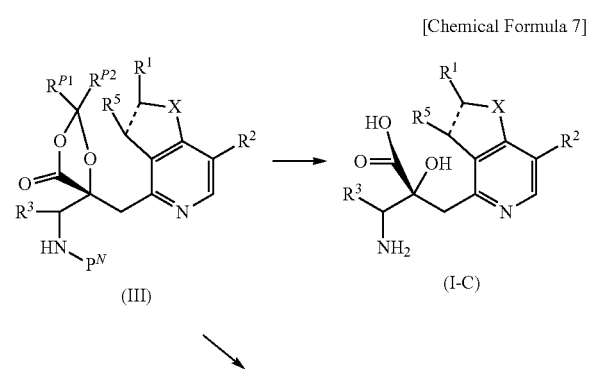

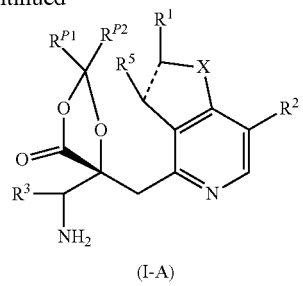

The compound (I-C) can be prepared by deprotection of the compound (III).

In this reaction, the compound (III) and a deprotecting reagent in equivalent amounts, or either thereof in an excess amount, are used, and the mixture is stirred for usually 0.1 hour to five days in a solvent which is inert to the reaction or in the absence of a solvent, under from cooling to heating with reflux. Examples of the solvent used herein are not particularly limited, but include alcohols such as methanol, ethanol and n-propanol; halogenated hydrocarbons such as dichloromethane, 1,2-dichloroethane and chloroform; 1,4-dioxane; N,N-dimethylformamide; tetrahydrofuran and the like. In some cases, a mixed solvent of such solvent(s) and water is preferably used for the reaction. Examples of the deprotecting reagent are not particularly limited, but include bases such as aqueous sodium hydroxide solution and aqueous potassium hydroxide solution; and acids such as hydrogen chloride and trifluoroacetic acid. In some cases, it is preferred to treat the compound (III) with a base and then with an acid, or to treat it with an acid and then with a base.

Examples of $P^N$, the protective group for an amino group, include tert-butoxycarbonyl, benzyloxycarbonyl, methoxymethyl, benzyloxymethyl and the like.

The compound (I-A) can also be prepared from the compound (III) under selected reaction conditions. For example, the compound (I-A) can be prepared by using tert-butoxycarbonyl as the protective group $P^N$ and treating with hydrogen chloride, trifluoroacetic acid and the like, in a solvent such as 1,4-dioxane or toluene.

(Other Production Process)

A compound of Formula (I) prepared by the respective production processes can be used as a starting material and is subjected to a chemical modification reaction generally used by those skilled in the art, such as esterification and amidation, to produce other compounds represented by Formula (I).

(Synthesis of Starting Material 1)

[Chemical Formula 8]

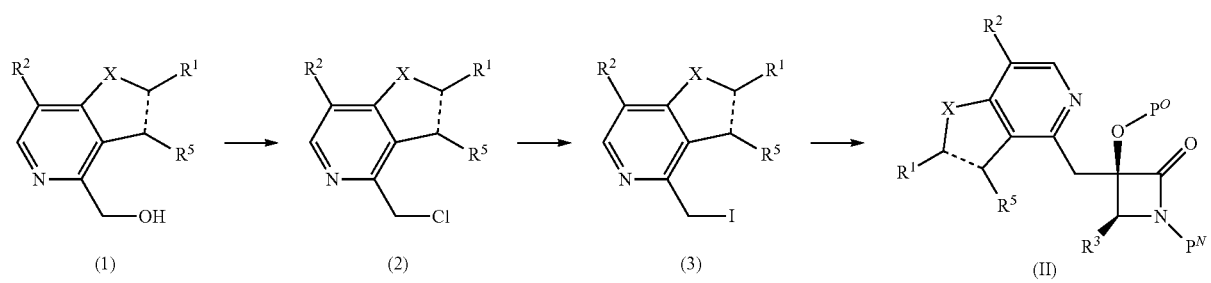

13

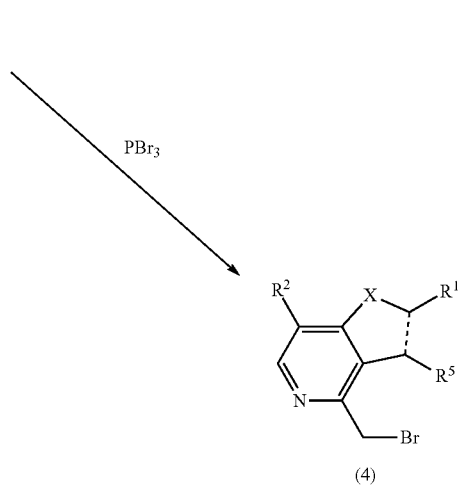

(4)

-continued

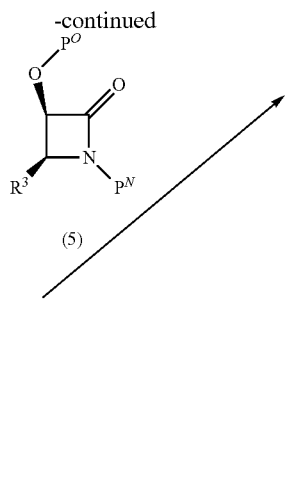

(5)

The compound (2) can be prepared through halogenation of a hydroxy group of the compound (1) using thionyl chloride and the like, and the compound (3) can be prepared through iodination of the compound (2) by Finkelstein reaction.

[Reference]

Chirality, 2011, 23(1), 24-33

The compound (II) can be prepared by reacting the compound (3) with the compound (5).

In this reaction, the compounds (3) and (5) in equivalent amounts, or either thereof in an excess amount, are used, the mixture is stirred for usually 0.1 hour to five days in a solvent which is inert to the reaction in the presence of a base under from cooling to room temperature, preferably under cooling. Examples of the solvent used herein are not particularly limited, but include aromatic hydrocarbons such as benzene, toluene and xylene; ethers such as diethylether, tetrahydrofuran, 1,4-dioxane and dimethoxyethane; hexane and a mixture thereof. Examples of the base include organic bases such as lithium diisopropylamide triethylamine, diisopropylethylamine, lithium hexamethyldisilazide, potassium hexamethyldisilazide, 1,8-diazabicyclo[5.4.0]-undec-7-ene, n-butyllithium and potassium tert-butoxide; and inorganic bases such as sodium carbonate, potassium carbonate, cesium carbonate and sodium hydride.

[Reference]

Journal of Organic Chemistry, 1990, 55(20), 5525-5528

Tetrahedron Letters, 2000, 41 (33), 6523-6526

Alternatively, the compound (II) can be prepared by reacting the compound (4), which is the brominated compound (1) with $PBr_3$, and the compound (5). In this reaction, the compounds (5) is treated with lithium diisopropylamide under argon atmosphere, the mixture is subsequently stirred for usually 1 hour to five days, under from cooling to room temperature, preferably under cooling, in a solvent which is inert to the reaction such as aromatic hydrocarbons such as benzene, toluene and xylene; ethers such as diethyl ether, tetrahydrofuran, 1,4-dioxane and 1,2-dimethoxyethane; halogenated hydrocarbons such as dichloromethane, 1,2-dichloroethane and chloroform.

[Reference]

Molecules, 2004, 9(5), 365-372

Tetrahedron Asymmetry, 1991, 2(7), 705-720

14

(Synthesis of Starting Material 2)

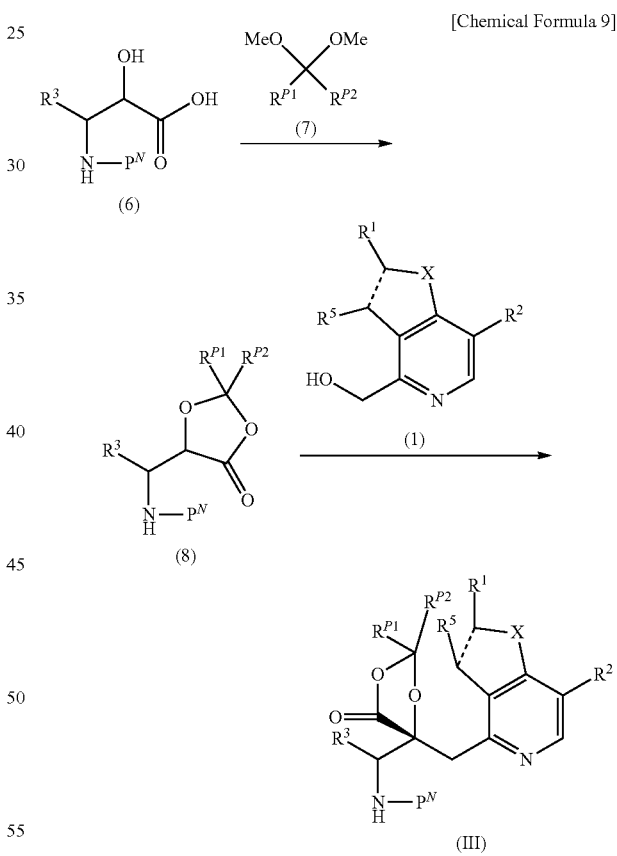

The compound (8) can be prepared by reacting the compound (6) with the compound (7) in the presence of pyridinium p-toluenesulfonate or p-toluenesulfonic acid. In this reaction, a mixture of the compounds (6) and (7) is stirred for one hour to five days in a solvent which is inert to the reaction in the presence of pyridinium p-toluenesulfonate or p-toluenesulfonic acid under from cooling to heating, preferably at a temperature of from 40 to 120° C. Examples of the solvent include aromatic hydrocarbons such as benzene, toluene and xylene; ethers such as diethylether, tetrahydrofuran, 1,4-dioxane and 1,2-dimethoxyethane; and halogenated hydrocarbons such as dichloromethane, 1,2-dichloroethane and chloroform.

Examples of $P^N$, the protective group for an amino group, include tert-butoxycarbonyl, benzyloxycarbonyl, methoxymethyl, benzyloxymethyl and the like.

(Synthesis of Other Starting Materials)

A desired starting compound can be prepared using any other method known to those skilled in the art. For example, the methods shown in the reaction scheme below can be used.

[Chemical Formula 10]

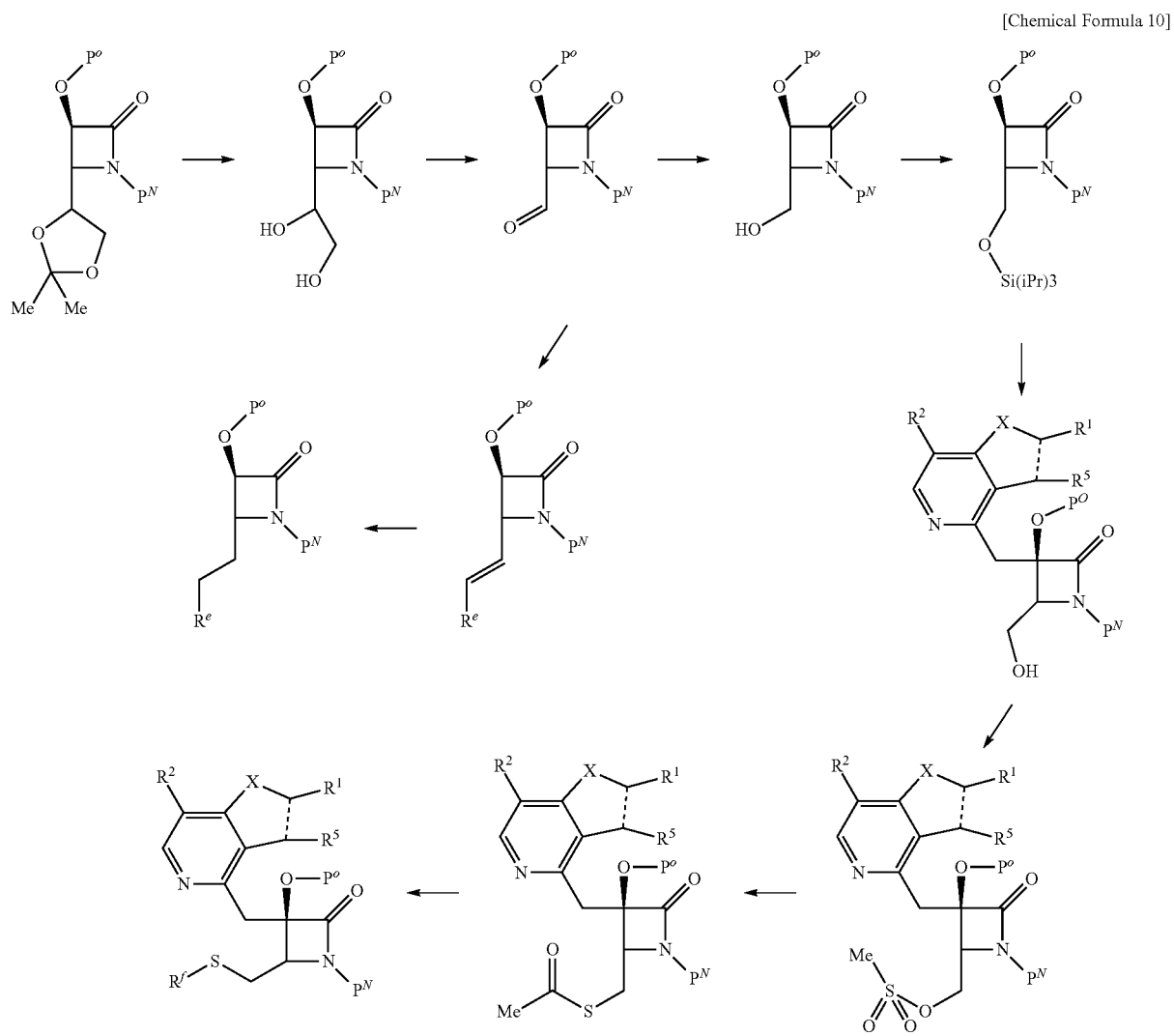

wherein $R^e$ and $R^f$ are each a group forming a part of $R^3$.

The compound (III) can be prepared by reacting the compound (8) with the compound (1). The reaction can be carried out by the same method as in the synthesis of the compound (II) from the compound (1) using the compound (5) described in Synthesis of Starting Material 1.

A compound (III) having a desired configuration can be prepared from a starting compound (6) in which the asymmetric carbon attached to —NHP$^N$ has a specific configuration. In some cases, it is preferred to add trimethylchlorosilane at the time of reaction of the compounds (8) and (1), depending on the configuration of the asymmetric carbon attached to —NHP$^N$. When a mixture in which the configurations of the asymmetric carbons attached to —NHP$^N$ are R and S is used as a starting compound, it is preferred to combine a general optical resolution technique.

The compounds represented by Formula (I) are isolated and purified as free bases, or salts, hydrates, solvates or crystalline polymorphs thereof. Salts of the compound represented by Formula (I) can also be prepared by a conventional salt forming reaction.

Isolation and purification is carried out by a general chemical procedure such as extraction, fractional crystallization, and various types of fractional chromatography.

Various isomers can be prepared by selection of appropriate starting compounds, or can be separated based on differences in physicochemical properties among the isomers. For example, optical isomers can be prepared by a general optical resolution technique of racemic products (for example, fractional crystallization that converts the compound into diastereomer salts with optically active bases or acids, or chromatography using a chiral column), or can also be prepared from appropriate optically active starting compounds.

Pharmacological effects of the compounds represented by Formula (I) were confirmed by the tests described below. Doses of individual test compounds described herein are indicated as corresponding weights of free bases.

(1) Inhibition of IRAP Activity

Rat epididymal fat pads were homogenized and subjected to ultracentrifugation at 100,000×g for 30 minutes to obtain microsomes containing IRAP. The microsomes (with a total protein content of 55 µg/well) were mixed with a solvent (dimethyl sulfoxide; hereinafter, abbreviated as DMSO (final concentration: 0.1%)) or with each test compound (common ratio: 3; maximum concentration: 10 µM). AVP was then added to the solution to a final concentration of 25 µM, and the resulting solution was allowed to react for one hour at 37° C. An aqueous trifluoroacetic acid (hereinafter, abbreviated as TFA) solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by the Sigmoid-Emax model nonlinear regression analysis to evaluate inhibition of IRAP activity.

The results are shown in Table 1, and indicate that the example compounds effectively inhibit AVP degradation by IRAP, i.e. a rat homolog of human P-LAP.

(2) Inhibition of Human P-LAP (hP-LAP) Activity

HEK293 cells forced to transiently express hP-LAP (J Biol Chem 1996; 271: 56-61) were prepared by lipofection, homogenized, and then subjected to ultracentrifugation at 100,000×g for 30 minutes. Microsomes containing hP-LAP were thereby prepared. The microsomes (with a total protein content of 0.5 to 1.5 µg/well) were mixed with a solvent (DMSO; final concentration: 0.1%) or with each test compound (common ratio: 3; maximum concentration: 10 µM). AVP was then added to the solution into a final concentration of 25 µM, and the resulting solution was allowed to react for one hour at 37° C. An aqueous TFA solution was then added to the solution (final concentration: 1%) to stop the enzymatic reaction. Residual AVP was then determined by mass spectrometry (MALDI-MS). Based on the results, $IC_{50}$ values (nM), i.e. concentrations required for 50% inhibition of decrease in AVP level in the solvent control group, of the individual test compounds were calculated by the Sigmoid-Emax model nonlinear regression analysis to evaluate inhibition of hP-LAP activity. The results are shown in Table 1 and indicate that the example compounds effectively inhibit AVP degradation by hP-LAP.

In the Tables 1 and 2 below, numerals in the column "Ex" indicate Example numbers related to the respective test compounds.

TABLE 1

| Ex | IRAP $IC_{50}$(nM) | hP-LAP $IC_{50}$(nM) |
| --- | --- | --- |
| 1 | 2.7 | 3.3 |
| 2 | 1.1 | 2.4 |
| 3 | 2.6 | 21 |
| 4 | 290 | 230 |
| 5 | 59 | 89 |
| 6 | 27 | 33 |
| 7(1) | 58 | 35 |

TABLE 1-continued

| Ex | IRAP $IC_{50}$(nM) | hP-LAP $IC_{50}$(nM) |
| --- | --- | --- |
| 7(2) | 8.4 | 7.0 |
| 8 | 8.8 | 7.0 |
| 9 | 3.4 | 4.1 |
| 10 | 82 | 75 |
| 11 | 9.2 | 3.6 |
| 12 | 5.7 | 8.0 |
| 13 | 1.6 | 4.3 |
| 14 | 0.80 | 3.9 |
| 15 | 1.9 | 6.0 |
| 16 | 0.56 | 6.9 |
| 17 | 4.3 | 14 |
| 18 | 2.6 | 7.9 |
| 19 | 94 | 200 |
| 20 | 130 | 140 |
| 21 | 6.6 | 7.0 |
| 22 | 36 | 27 |
| 23 | 4.6 | 4.9 |
| 24 | 7.4 | 16 |
| 25 | 7.2 | 4.4 |
| 26 | 2.1 | 3.1 |
| 27 | 3.7 | 4.2 |

(3) Antidiuresis Test in Water-Loaded Rats (Oral Administration)

Individual test compounds were dissolved in a vehicle (containing 10% N,N-dimethylformamide, 10% propylene glycol, and 80% distilled water), and the resulting solution was orally administered to the rats. When a test compound is a free base, one molar equivalent hydrochloric acid was added to dissolve the compound in the solvent. Rats in a vehicle control group were administered only with the vehicle. One hour after the administration, 30 ml/kg of distilled water was orally administered to the rats. One hour after the water loading, the urine volume was measured (urine volumes less than 0.3 ml were considered as 0 ml) to calculate the ratio of the urine volume (urinary excretion rate) to the amount of water load. The inhibition of urination (%) in the compound-administered group in comparison with the vehicle control group was calculated in accordance with the following expression (each group consisted of four to five rats):

Inhibition of urination (%)={[(urinary excretion rate in the vehicle control group)−(urinary excretion rate in the compound-administered group]/(urinary excretion rate in the vehicle control group)}×100

Table 2 shows inhibition of urination (%) observed when some example compounds included in compounds of Formula (I) were respectively administered in the amount of 3 mg/kg. The results indicate that the example compounds have an excellent antidiuretic effect.

TABLE 2

| Ex | Inhibition (%) |
| --- | --- |
| 1 | 98 |
| 2 | 98 |
| 8 | 72 |
| 9 | 97 |
| 12 | 82 |
| 14 | 98 |
| 16 | 100 |
| 17 | 72 |
| 21 | 68 |

TABLE 2-continued

| Ex | Inhibition (%) |
|---|---|
| 23 | 78 |
| 26 | 96 |
| 27 | 87 |

The results shown above suggest that the compounds represented by Formula (I) inhibit P-LAP (IRAP), i.e. an aminopeptidase that cleaves AVP, to inhibit degradation of endogenous AVP, which results in a reduced urine production.

It is known that the plasma AVP level is strictly regulated by plasma osmolality and that an excessive water intake reduces AVP production and secretion to cause diuresis. The present inventors had obtained the results, from the antidiuresis test in continuously hydrated rats with additional water loading using the compounds having an antidiuretic effect based on P-LAP inhibition, revealing that in a case of an excessive water intake caused by the additional water loading, reduced urine volumes were recovered (PCT/JP2015/065344). It is suggested that the decreased endogenous AVP level caused by the additional water loading reduces the antidiuretic effect. Therefore, the compound represented by Formula (I) having the antidiuretic effect based on P-LAP inhibition is expected to be an agent for treating nocturia involving lower risks of hyponatremia even in a case of an excessive water intake, unlike V2 receptor agonists which requires attention for hyponatremia.

A pharmaceutical composition containing one or more compounds represented by Formula (I) or salts thereof as an active ingredient can be prepared by a common method using an excipient generally used in the art, that is, an excipient or a carrier for a pharmaceutical.

Such a pharmaceutical composition can be administered in any form, such as oral administration of tablets, pills, capsules, granules, powder, or liquid, and parental administration by intraarticular, intravenous, or intramuscular injection, suppositories, transdermal liquid, transdermal patches, transmucosal liquid, transmucosal patches, or inhalations.

A solid composition for oral administration may be in a form of, for example, a tablet, powder, and granules. Such a solid composition contains one or more active ingredients mixed with at least one inactive excipient. The composition may contain an inactive additive, for example, a lubricant, a disintegrating agent, a stabilizing agent, and a solubilizing agent, in accordance with conventional techniques. Tablets or pills may be coated with sugar or a film of gastric or enteric soluble material, if necessary.

A liquid composition for oral administration includes a pharmaceutically acceptable emulsion, solution, suspension, syrup, and elixir, and contains a common inactive diluent, for example, purified water or ethanol. The liquid composition may contain an additive such as a solubilizing agent, a moisturizer, and a suspending agent; a sweetening agent; a flavoring agent; an aromatic agent; and a preservative, in addition to the inactive diluent.

An injection for parenteral administration contains aqueous or non-aqueous sterile solvent, suspension, or emulsion. Examples of the aqueous solvent include distilled water for injection and physiological saline. Examples of the non-aqueous solvent include alcohols such as ethanol. The composition may further contain a tonicity agent, a preservative, a moisturizer, an emulsifier, a dispersant, a stabilizer, or a solubilizing agent. These components are sterilized by filtration through a bacteria retentive filter, blending a bactericide, or irradiation, for example. These components may also be formulated into a sterile solid composition to be dissolved or suspended in a sterile solvent for injection before use.

If the compound represented by Formula (I) is orally administered, an appropriate daily dose is approximately 0.001 to 100 mg/kg, preferably 0.1 to 30 mg/kg, more preferably 0.1 to 10 mg/kg, per body weight, and is administered daily in a single dose or in two to four separate doses. If the compound is intravenously administered, an appropriate daily dose is approximately 0.0001 to 10 mg/kg per body weight, and is administered daily in a single dose or in separate doses. If the compound is transmucosally administered, an appropriate daily dose is approximately 0.001 to 100 mg/kg per body weight, and is administered daily in a single dose or in separate doses. The dose is appropriately determined depending on, for example, the symptom, age, and sex of individual patient. If the compound represented by Formula (I) is used for prevention or treatment of nocturia, it may be preferably administered once daily after supper or before going to bed, for example.

The pharmaceutical composition of the present invention contains one or more compounds represented by Formula (I) or salts thereof in an amount of 0.01 to 100% by weight, in one embodiment 0.01 to 50% by weight, as an active ingredient, while the amount may vary depending on a route of administration, dosage form, site of administration, and the type of excipient or additive.

The compound represented by Formula (I) may be used in combination with various therapeutic agents or preventive agents for diseases to which the compound of Formula (I) is assumed to be effective. The compound represented by Formula (I) and the agent to be used in combination therewith may be administered simultaneously, sequentially or at desired time intervals. The preparation to be simultaneously administered may be combined with the compound of Formula (I) or formulated as a separate preparation.

EXAMPLES

Hereinbelow, the production processes for the compound represented by Formula (I) will be described in more details with reference to Examples. The present invention is not limited to the compounds described in the Examples. Production processes for starting compounds will be described in Production Examples. The production process for the compound represented by Formula (I) should not be limited to the processes described in the specific Examples and Production Examples below, but the compound represented by Formula (I) can be prepared by a combination of such production processes or by any method obvious to those skilled in the art.

As used herein, the unit "mol/L" for a concentration is abbreviated as "M" for expediency. For example, "1M aqueous sodium hydroxide solution" refers to 1 mol/L aqueous sodium hydroxide solution.

In the Examples, Production Examples and Tables below, the following abbreviations may be used:

DMF: N,N-dimethylformamide; AcOEt: ethyl acetate; AcOH: acetic acid; THF: tetrahydrofuran; MeCN: acetonitrile; EtOH: ethanol; MeOH: methanol; DOX: 1,4-dioxane; TFA: trifluoroacetic acid; Et$_3$N: triethylamine; DIPEA: diisopropylethylamine; Pd/C: palladium on carbon; NaBH$_4$: sodium borohydride; LDA: lithium diisopropylamide; ODS: octadecylsilyl; PEx: Production Example number; Ex: Example number; PSyn: the Production Example number in which a compound is prepared by the same method; Syn: Example number in which a compound is prepared by the same method; Str: chemical structural formula; Boc: tert-butoxycarbonyl, TIPS: triisopropylsilyl, DATA: physicochemical data, ESI+: m/z value in mass spectrometry (electrospray ionization (ESI); representing [M+H]$^+$ unless otherwise specified); ESI−: m/z value in mass spectrometry (electrospray ionization (ESI); representing [M−H]$^-$ unless otherwise specified); APCI/ESI+: APCI/ESI-MS (atmospheric-pressure chemical ionization (APCI); APCI/ESI indicates simultaneous measurement by APCI and ESI; representing [M+H]$^+$ unless otherwise specified); and CI+: m/z value in mass spectrometry (chemical ionization (CI); representing [M+H]$^+$ unless otherwise specified). The "HCl" in a structural formula indicates that the compound is a monohydrochloride, and the "2HCl" indicates that the compound is a dihydrochloride. A double bond represented with two crossed lines in a chemical formula indicates that the double bond forms an E isomer or Z isomer, or a mixture thereof.

The compound represented by Formula (I) to be described in Examples later has at least two asymmetric carbon atoms, and among them, the carbon atom (position 2) to which carboxy group is attached has the (R) configuration. The symbol "*" in a chemical structural formula indicates that the corresponding compound is a single isomer having the indicated configuration. The symbol "#1" indicates that the corresponding compound has the indicated steric configuration and is a mixture of isomers which have (R) and (S) configurations, respectively, in an asymmetric carbon with the steric configuration not indicated. The symbol "#2" indicates that the corresponding compound has the indicated configuration and is a mixture of isomers which have (R) and (S) configurations, respectively, in the sulfoxide moiety.

In the present specification, a nomenclature software such as ACD/Name (registered trademark, Advanced Chemistry Development, Inc.) may be used for nomenclature of compounds in some cases.

RINT-TTRII was used in the measurement of powder X-ray diffraction described herein. The diffractometry was carried out under the following conditions: X-ray tube: Cu; tube current: 300 mA; tube voltage: 50 kV; sampling width: 0.020°; scanning speed: 4°/min; wavelength: 1.54056 Å; range of diffraction angle in measurement (2θ): 2.5 to 40°. In powder X-ray diffraction, the crystal lattice distance and the entire pattern are important for the identification of crystals in view of the characteristics of the data. A diffraction angle and intensity may slightly vary depending on the direction of crystal growth, the particle size, and the measuring conditions, and should not be interpreted strictly. As used herein, the diffraction angle (2θ) in the powder X-ray diffraction pattern is interpreted with a margin of error generally acceptable in the measurement, for example, a margin of error of ±0.2°.

Example 1

A mixture of (3R,4R)-3-{[2-(2-cyclopropylethyl)furo[3,2-c]pyridin-4-yl]methyl}-4-[(ethylsulfanyl)methyl]-3-(methoxymethoxy)-1-(methoxymethyl)azetidin-2-one (65 mg), DOX (0.75 ml) and 6 M hydrochloric acid (1.5 ml) was stirred at 60° C. for 1.5 hours. After cooling the resulting reaction mixture with an ice-water bath, 6 M aqueous sodium hydroxide solution (1 ml) and DOX were added thereto and the mixture was concentrated under reduced pressure. The resulting residue was purified by ODS column chromatography (MeCN/0.1% aqueous formic acid solution) to give (2R,3R)-3-amino-2-{[2-(2-cyclopropylethyl)furo[3,2-c]pyridin-4-yl]methyl}-4-(ethyl sulfanyl)-2-hydroxybutanoic acid (39 mg) as a solid.

Example 2

TFA (25 ml) was added to a mixture of tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (6 g) and CH$_2$Cl$_2$ (50 ml) under ice-bath cooling, and the mixture was stirred at room temperature for 1 hour. The resulting reaction mixture was slowly added to a mixture of MeOH (85 ml) and 6 M aqueous sodium hydroxide solution (77 ml) under ice-bath cooling, and subsequently the mixture was stirred at 60° C. for 1.5 hours. Activated carbon was added to the obtained reaction mixture, the mixture was stirred at room temperature for 30 minutes and subsequently the insoluble material was removed by filtration. After cooling the obtained filtrate with an ice-water bath, 6 M hydrochloric acid was slowly added thereto to adjust pH to about 7, and subsequently the mixture was stirred at the same temperature for 1 hour. The produced insoluble material was collected by filtration and dried under reduced pressure. To the obtained solid, a mixture (45 ml) of EtOH:water (3:1) was added, the mixture was heated to 80° C. and stirred until the solid was dissolved, and then water (30 ml) was added thereto. The obtained solution was gradually allowed to cool to room temperature and stirred overnight. The precipitated solid was collected by filtration to give (2R,3R)-3-amino-2-{[2-(2-cyclopropylethyl)furo[3,2-c]pyridin-4-yl]methyl}-2-hydroxy-4-(methylsulfanyl)butanoic acid (2.43 g) as a crystal. The obtained crystal had a powder X-ray diffraction pattern having peaks at 2θ (°) 6.5, 8.6, 12.3, 14.1, 14.7, 17.4, 17.9, 18.5, 19.1, 19.6, 20.7, 22.7 and 24.8.

Example 3

A 6 M aqueous sodium hydroxide solution (2 ml) was added to a mixture of (3R,4R)-3-{[2-(2-cyclopropylethyl)furo[3,2-c]pyridin-4-yl]methyl}-4-[(isopropyl sulfanyl)methyl]-3-(methoxymethoxy)-1-(methoxymethyl)azetidin-2-one (71 mg), MeOH (2 ml) and THF (2 ml) and the mixture was stirred at 70° C. for 5 hours. 6 M Hydrochloric acid (2 ml) was added to the obtained reaction mixture under ice-bath cooling and the mixture was concentrated under reduced pressure. MeCN (1 ml) and 1 M hydrochloride acid (3 ml) were added to the obtained residue and the mixture was stirred at room temperature for 3 hours. 6 M Hydrochloric acid (0.5 ml) was added to the obtained reaction mixture, the mixture was stirred at room temperature for 18 hours and subsequently at 40° C. for 2 hours. The reaction mixture was allowed to cool to room temperature and water was added thereto. The obtained mixture was concentrated under reduced pressure and the residue was purified by ODS column chromatography (MeCN/0.1% aqueous formic acid solution) to give (2R,3R)-3-amino-2-{[2-(2-cyclopropylethyl)furo[3,2-c]pyridin-4-yl]methyl}-2-hydroxy-4-(isopropylsulfanyl)butanoic acid (21 mg) as a solid.

Example 4

TFA (5 ml) was added to a mixture of tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (1.1 g) and toluene (15 ml) at room temperature, and the mixture was stirred at the same temperature overnight. The obtained reaction mixture was concentrated under reduced pressure, a saturated aqueous sodium hydrogen carbonate solution was added to the residue, and the mixture was extracted with AcOEt. The obtained organic layer was dried over anhydrous magnesium sulfate and the solvent was concentrated under reduced pressure. The resulting residue was purified by silica gel column chromatography (CHCl$_3$/MeOH) to give (5R)-5-[(1R)-1-amino-2-(methylsulfanyl)ethyl]-5-{[2-(2-cyclopropylethyl)furo[3,2-c]pyridin-4-yl]methyl}-2,2-dimethyl-1,3-dioxolan-4-one (777 mg) as an oily product.

1 M Hydrochloric acid (1 ml) was added to the resulting (5R)-5-[(1R)-1-amino-2-(methylsulfanyl)ethyl]-5-{[2-(2-cyclopropylethyl)furo[3,2-c]pyridin-4-yl]methyl}-2,2-dimethyl-1,3-dioxolan-4-one (65 mg) and subsequently the solvent was distilled off under reduced pressure to give (5R)-5-[(1R)-1-amino-2-(methylsulfanyl)ethyl]-5-{[2-(2-cyclopropylethyl)furo[3,2-c]pyridin-4-yl]methyl}-2,2-dimethyl-1,3-dioxolan-4-one dihydrochloride (70 mg) as a foamy solid.

Example 5

A mixture of (5R)-5-[(1R)-1-amino-2-(methylsulfanyl)ethyl]-5-{[2-(2-cyclopropylethyl)furo[3,2-c]pyridin-4-yl]methyl}-2,2-dimethyl-1,3-dioxolan-4-one (95 mg), MeOH (5 ml) and potassium carbonate (200 mg) was stirred at room temperature for 12 hours. AcOEt was added to the resulting reaction mixture to remove insoluble materials by filtration. The obtained filtrate was concentrated under reduced pressure and the residue was purified by silica gel column chromatography (CHCl$_3$/MeOH). 1 M Hydrochloric acid (1 ml) was added to the resulting product and the solvent was distilled off under reduced pressure to give (2R,3R)-3-amino-2-{[2-(2-cyclopropylethyl)furo[3,2-c]pyridin-4-yl]methyl}-2-hydroxy-4-(methylsulfanyl)methyl butanoate dihydrochloride (55 mg) as a foamy solid.

Example 6

A mixture of (5R)-5-[(1R)-1-amino-2-(methylsulfanyl)ethyl]-5-{[2-(2-cyclopropylethyl)furo[3,2-c]pyridin-4-yl]methyl}-2,2-dimethyl-1,3-dioxolan-4-one (98 mg), MeOH (2 ml) and 28% ammonia water (2 ml) was stirred at 120° C. for 30 minutes under microwave irradiation. Water was added to the resulting reaction mixture and the mixture was extracted with a 1:1 mixture of AcOEt and toluene. The obtained organic layer was dried over anhydrous magnesium sulfate and the solvent was concentrated under reduced pressure. The resulting residue was purified by silica gel column chromatography (CHCl$_3$/MeOH). 1 M Hydrochloric acid (1 ml) was added to the resulting product and the solvent was distilled off under reduced pressure to give (2R,3R)-3-amino-2-{[2-(2-cyclopropylethyl)furo[3,2-c]pyridin-4-yl]methyl}-2-hydroxy-4-(methylsulfanyl)butanamide dihydrochloride (20 mg) as a foamy solid.

Example 7

Concentrated hydrochloric acid (5 ml) was added to tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-methylsulfanyl)ethyl]carbamate (400 mg), and the mixture was stirred at 80° C. for 3 days. The resulting reaction mixture was purified by ODS column chromatography (MeCN/0.1% aqueous formic acid solution) to give, one of the obtained two kinds of the compounds, (1) (2R,3R)-3-amino-2-hydroxy-2-{[2-(3-hydroxypentyl)furo[3,2-c]pyridin-4-yl]methyl}-4-(ethylsulfanyl)butanoic acid (65 mg) as a foamy solid of a high polar compound. 1 M Hydrochloric acid (2 ml) was added to the other product obtained as a low polar compound and subsequently the solvent was distilled off under reduced pressure to give (2) (2R,3R)-3-amino-2-{[2-(3-chloropentyl)furo[3,2-c]pyridin-4-yl]methyl}-2-hydroxy-4-(methylsulfanyl)butanoic acid dihydrochloride (107 mg) as a foamy solid.

Example 8

A 1 M aqueous sodium hydroxide solution (0.83 ml) was added to a mixture of tert-butyl [(1R)-1-{(4R)-4-[(2-butylthieno[3,2-c]pyridin-4-yl)methyl]-2,2-dimethyl-5-oxo-1,3-dioxolan-4-yl}-2-(methylsulfanyl)ethyl]carbamate (83 mg), MeOH (0.83 ml) and DOX (0.83 ml) and the mixture was stirred at 50° C. for 5 hours. The reaction mixture was allowed to cool to room temperature and concentrated under reduced pressure. After adding DOX (0.83 ml) to the resulting residue, hydrogen chloride (4M DOX solution, 0.83 ml) was added thereto under ice-bath cooling. The resulting mixture was stirred at room temperature for 1.5 hours and concentrated under reduced pressure. The resulting residue was purified by ODS column chromatography (MeCN/0.1% aqueous formic acid solution) to give a solid. The resulting solid was suspended in MeCN-MeOH (10:1) and the insoluble materials were collected by filtration. The collected solid was washed with MeCN to give (2R,3R)-3-amino-2-[(2-butylthieno[3,2-c]pyridin-4-yl)methyl]-2-hydroxy-4-(methylsulfanyl)butanoic acid (27 mg) as a solid.

Example 9

TFA (0.635 ml) was added to a mixture of tert-butyl [(1R)-1-[(4R)-2,2-dimethyl-4-{[(2-(3-methylbutyl)furo[3,2-c]pyridin-4-yl]methyl}-5-oxo-1,3-dioxolan-4-yl]-2-(methylsulfanyl)ethyl]carbamate (140 mg) and CH$_2$Cl$_2$ (1.4 ml), and the mixture was stirred at room temperature for 2 hours. The resulting reaction mixture was slowly added to a mixture of MeOH (2.1 ml) and 6 M aqueous sodium hydroxide solution (1.85 ml) under ice-bath cooling, and subsequently the mixture was stirred at 60° C. for 3 hours. 6 M Hydrochloric acid (0.46 ml) was added to the obtained reaction mixture under ice-bath cooling, and the mixture was stirred at room temperature for 10 minutes. The resulting solution was purified by ODS column chromatography (MeCN/0.1% aqueous formic acid solution). An excess amount of 1 M hydrochloric acid was added to the obtained product and subsequently the solvent was distilled off under reduced pressure to give (2R,3R)-3-amino-2-hydroxy-2-{[2-(3-methylbutyl)furo[3,2-c]pyridin-4-yl]methyl}-4-(methylsulfanyl)butanoic acid dihydrochloride (100 mg) as a solid.

Example 10

A mixture of (3R,4R)-3-[(2,3-diethylfuro[3,2-c]pyridin-4-yl)methyl]-4-[(ethylsulfanyl)methyl]-3-(methoxymethoxy)-1-(methoxymethyl)azetidin-2-one (95 mg), DOX (0.95 ml) and 6M hydrochloric acid (0.73 ml) was stirred at 60° C. for 3 hours. A 1 M aqueous sodium hydroxide solution was added to the obtained reaction mixture under ice-bath cooling to neutralize the mixture. The resulting mixture was purified by ODS column chromatography (MeCN/0.1% aqueous formic acid solution). An excess amount of 1 M hydrochloric acid was added to the obtained product and subsequently the solvent was distilled off under reduced pressure to give (2R,3R)-3-amino-2-[(2,3-diethylfuro[3,2-c]pyridin-4-yl)methyl]-4-(ethylsulfanyl)-2-hydroxy butanoic acid dihydrochloride (75 mg) as a solid.

Example compounds shown in Tables to be described later were produced in the same manner as in the method described in any of the above Examples. Tables to be described later show the structure, physicochemical data and production method of the Example compounds.

Production Example 1

A mixture of (3R,4R)-4-[(4S)-2,2-dimethyl-1,3-dioxolan-4-yl]-3-hydroxy-1-(4-methoxyphenyl)azetidin-2-one (21.94 g), 1,2-dichloroethane (300 ml), chloro(methoxy)methane (23.6 ml) and DIPEA (70 ml) was stirred at 110° C. for 12 hours. Water was added to the obtained reaction mixture and the mixture was extracted with $CHCl_3$. The obtained organic layer was dried over anhydrous magnesium sulfate and the organic layer was concentrated under reduced pressure. The obtained solid was washed with a mixture of diisopropyl ether and MeOH to give (3R,4S)-4-[(4S)-2,2-dimethyl-1,3-dioxolan-4-yl]-3-(methoxymethoxy)-1-(4-methoxyphenyl)azetidin-2-one (12.30 g) as a solid. The obtained filtrate was concentrated and the residue was purified by silica gel column chromatography ($CHCl_3$/MeOH) to give the same compound (12.75 g) as a solid.

Production Example 2

Ammonium cerium (IV) nitrate (6.3 g) was added to a mixture of (3R,4S)-4-(2-cyclopropylethyl)-3-(methoxymethoxy)-1-(4-methoxyphenyl)azetidin-2-one (1.24 g), MeCN (30 ml) and water (15 ml) under ice-bath cooling and the mixture was stirred for 30 minutes. Water and a saturated aqueous sodium hydrogen carbonate solution were added to the resulting reaction mixture with stirring and subsequently 2% aqueous sodium hydrogen sulfite solution was added thereto. The resulting reaction mixture was filtered through Celite pad and the filtrate was extracted with $CHCl_3$. The obtained organic layer was washed with a saturated aqueous sodium chloride solution, dried over anhydrous magnesium sulfate and subsequently concentrated under reduced pressure. The resulting residue was purified by silica gel column chromatography (hexane/AcOEt) to give (3R,4S)-4-(2-cyclopropylethyl)-3-(methoxymethoxy)azetidin-2-one (601 mg) as a solid.

Production Example 3

Potassium hexamethyldisilazide (1.0 M THF solution, 1.5 ml) was added to a mixture of (3R,4S)-4-[(4S)-2,2-dimethyl-1,3-dioxolan-4-yl]-3-(methoxymethoxy)azetidin-2-one (302 mg), chloro(methoxy)methane (0.15 ml), tetra-n-butylammonium iodide (500 mg) and THF (9 ml) under ice-bath cooling, the mixture was stirred for 1 hour and then stirred at room temperature overnight. Water was added to the resulting reaction mixture and the mixture was extracted with AcOEt. The obtained organic layer was dried over anhydrous magnesium sulfate and concentrated under reduced pressure. The resulting residue was purified by silica gel column chromatography (hexane/AcOEt) to give (3R,4S)-4-[(4S)-2,2-dimethyl-1,3-dioxolan-4-yl]-3-(methoxymethoxy)-1-(methoxymethyl)azetidin-2-one (247 mg) as an oily product.

Production Example 4

A mixture of (3R,4S)-4-[(4S)-2,2-dimethyl-1,3-dioxolan-4-yl]-3-(methoxymethoxy)-1-(4-methoxyphenyl)azetidin-2-one (3.17 g), AcOH (50 ml) and water (13 ml) was stirred at 50° C. for 4 hours. The resulting reaction mixture was allowed to cool to room temperature and subsequently concentrated under reduced pressure. The resulting residue was purified by silica gel column chromatography ($CHCl_3$/MeOH) to give (3R,4S)-4-[(1S)-1,2-dihydroxyethyl]-3-(methoxymethoxy)-1-(4-methoxyphenyl)azetidin-2-one (2.57 g) as an oily product.

Production Example 5

Sodium periodate (2.3 g) was added to a mixture of (3R,4S)-4-[(1S)-1,2-dihydroxyethyl]-3-(methoxymethoxy)-1-(4-methoxyphenyl)azetidin-2-one (2.09 g), $CH_2Cl_2$ (40 ml) and a saturated aqueous sodium hydrogen carbonate solution (1 ml) and the mixture was stirred at room temperature for 1 hour. Anhydrous magnesium sulfate was added to the resulting reaction mixture and the mixture was stirred for 30 minutes. The resulting reaction mixture was filtered through Celite pad and concentrated under reduced pressure to give (2R,3R)-3-(methoxymethoxy)-1-(4-methoxyphenyl)-4-oxoazetidin-2-carbaldehyde (1.80 g) as a solid.

Production Example 6

$NaBH_4$ (1.2 g) was added to a mixture of (2R,3R)-3-(methoxymethoxy)-1-(methoxymethyl)-4-oxoazetidin-2-carbaldehyde (5.08 g) and THF (50 ml) under ice-bath cooling and the mixture was stirred for 30 minutes. After adding water (5 ml) to the resulting reaction mixture, anhydrous magnesium sulfate was added thereto and the mixture was stirred at room temperature for 30 minutes. The resulting reaction mixture was filtered and subsequently the filtrate was concentrated under reduced pressure. The resulting residue was purified by silica gel column chromatography ($CHCl_3$/MeOH) to give (3R,4S)-4-(hydroxymethyl)-3-(methoxymethoxy)-1-(methoxymethyl)azetidin-2-one (4.43 g) as an oily product.

Production Example 7

A mixture of (3R,4S)-4-(hydroxymethyl)-3-(methoxymethoxy)-1-(methoxymethyl)azetidin-2-one (100 mg), triisopropylchlorosilane (0.21 ml), imidazole (140 mg) and DMF (2 ml) was stirred at room temperature overnight. The resulting reaction mixture was added to water and the mixture was extracted with AcOEt. The obtained organic layer was washed with a saturated aqueous sodium chloride solution, dried over anhydrous magnesium sulfate and subsequently concentrated under reduced pressure. The resulting residue was purified by silica gel column chromatography (hexane/AcOEt) to give (3R,4S)-3-(methoxymethoxy)-1-(methoxymethyl)-4-{[(triisopropylsilyl)oxy]methyl}azetidin-2-one (137 mg) as an oily product.

Production Example 8

A solution of $PBr_3$ (0.25 ml) in THF (3 ml) was added to a mixture of [2-(2-cyclopropylethyl)furo[3,2-c]pyridin-4-yl]methanol (850 mg) and THF (24 ml) under ice-bath cooling, and subsequently the mixture was stirred at room temperature for 3 hours. The resulting reaction mixture was poured into a mixture of a saturated aqueous sodium hydrogen carbonate solution and $CH_2Cl_2$ cooled with ice-water bath, and the obtained mixture was stirred at room temperature for 5 minutes. The organic layer was separated and the aqueous layer was extracted with $CH_2Cl_2$. The obtained organic layers were combined and dried over anhydrous magnesium sulfate. The obtained organic layer was diluted with toluene and concentrated under reduced pressure to about 5 ml. The obtained mixture was diluted again with toluene and concentrated under reduced pressure to about 5 ml (Mixture A). Under nitrogen atmosphere, LDA (1.09 M hexane-THF solution, 4.5 ml) was added slowly to a solution of (3R,4S)-3-(methoxymethoxy)-1-(methoxymethyl)-4-{[(triisopropylsilyl)oxy]methyl}azetidin-2-one (1.2 g) in THF (20 ml) at −78° C. and the mixture was stirred for 30 minutes. The mixture A was added dropwise to the obtained reaction mixture and subsequently the mixture was stirred at the same temperature for 1.5 hours. A saturated aqueous ammonium chloride solution was added to the resulting reaction mixture, and subsequently the mixture was allowed to warm up to room temperature and extracted twice with AcOEt. The obtained organic layer was dried over anhydrous magnesium sulfate and concentrated under reduced pressure. The resulting residue was purified by silica gel column chromatography ($CHCl_3$/AcOEt) to give (3R,4S)-3-{[2-(2-cyclopropylethyl)furo[3,2-c]pyridin-4-yl]methyl}-3-(methoxymethoxy)-1-(methoxymethyl)-4-{[(triisopropylsilyl)oxy]methyl}azetidin-2-one (1.6 g) as an oily product.

Production Example 9

Under argon atmosphere, a mixture of 5-[(cyclopropylmethyl) sulfonyl]-1-phenyl-1H-tetrazole (3.32 g) and THF (60 ml) was cooled to −78° C., lithium hexamethyldisilazide (1.3 M THF solution, 11 ml) was added thereto and the mixture was stirred for 30 minutes. A solution of (2R,3R)-3-(methoxymethoxy)-1-(4-methoxyphenyl)-4-oxoazetidine-2-carbaldehyde (3.00 g) was added to the resulting reaction mixture and the mixture was stirred at the same temperature for 30 minutes. The resulting reaction mixture was allowed to warm up to room temperature. A saturated aqueous ammonium chloride solution was added to the mixture and the mixture was extracted with AcOEt. The obtained organic layer was washed with a saturated aqueous sodium chloride solution and dried over anhydrous magnesium sulfate. The organic layer was concentrated under reduced pressure and the resulting residue was purified by silica gel column chromatography (hexane/AcOEt) to give (3R)-4-(2-cyclopropylvinyl)-3-(methoxymethoxy)-1-(4-methoxyphenyl)azetidin-2-one (1.73 g) as a solid.

Production Example 10

$PtO_2$ (61 mg) was added to a solution of (3R)-4-(2-cyclopropylvinyl)-3-(methoxymethoxy)-1-(4-methoxyphenyl)azetidin-2-one (831 mg) in toluene (25 ml) and the mixture was stirred at 0° C. for 6 hours under hydrogen atmosphere. Insoluble material was removed by filtration from the resulting reaction mixture and subsequently the filtrate was concentrated under reduced pressure. The resulting residue was purified by silica gel column chromatography (hexane/AcOEt) to give (3R,4S)-4-(2-cyclopropylethyl)-3-(methoxymethoxy)-1-(4-methoxyphenyl)azetidin-2-one (574 mg) as an oily product.

Production Example 11

(1,5-Cyclooctadiene)(pyridine)(tricyclohexylphosphine) iridium (I) hexafluorophosphate (270 mg) was added to a mixture of (3R)-4-(2-cyclobutylvinyl)-3-(methoxymethoxy)-1-(4-methoxyphenyl)azetidin-2-one (1.06 g) and $CH_2Cl_2$ (24 ml) and the mixture was stirred at room temperature overnight under hydrogen atmosphere. The resulting reaction mixture was concentrated under reduced pressure and the resulting residue was purified by silica gel column chromatography (hexane/AcOEt) to give (3R,4S)-4-(2-cyclobutylethyl)-3-(methoxymethoxy)-1-(4-methoxyphenyl)azetidin-2-one (960 mg) as an oily product.

Production Example 12

A mixture of tert-butyl [(2R)-1-(methylsulfanyl)-3-oxopropan-2-yl]carbamate (20 g), water (13 ml) and MeCN (54 ml) was added dropwise to a solution of sodium hydrogen sulfite (19 g) in water (130 ml) under ice-bath cooling, and the mixture was stirred at room temperature for 13 hours. To the reaction mixture was added Methyl-tert-butyl ether with stirring, the aqueous layer and the organic layer were separated. Further, the organic layer was extracted with water and the obtained water layer was combined with the previously obtained aqueous layer. To the combined aqueous layers were added AcOEt (100 ml) and potassium cyanide (7.7 g), and the mixture was stirred at room temperature for 18 hours. The organic layer was separated from the obtained reaction mixture and the aqueous layer was extracted twice with AcOEt. The obtained organic layers were combined, subsequently washed with an aqueous sodium hydrogen carbonate solution and a saturated aqueous sodium chloride solution and dried over anhydrous sodium sulfate. The solvent was distilled off under reduced pressure to give tert-butyl [(2R)-1-cyano-1-hydroxy-3-(methylsulfanyl)propan-2-yl]carbamate (17.2 g) as an oily product.

Production Example 13

Under ice-bath cooling, concentrated hydrochloric acid (70 ml) was slowly added to tert-butyl [(2R)-1-cyano-1-hydroxy-3-(methylsulfanyl)propan-2-yl]carbamate (17.2 g), and the mixture was stirred at 90° C. for 2 hours. The procedure, in which the resulting reaction mixture was concentrated under reduced pressure, toluene was added to the residue and the solvent was distilled off under reduced pressure, was repeated five times to give a residue (18 g) containing (3R)-3-amino-2-hydroxy-4-(methylsulfanyl)butanoic acid hydrochloride as an oily product.

Production Example 14

2-(Tert-butoxycarbonyloxyimino)-2-phenylacetonitrile (42 g) was added to a mixture of (3R)-3-amino-2-hydroxy-4-(methylsulfanyl)butanoic acid hydrochloride (18 g), THF (90 ml), water (90 ml), 4-dimethylamino pyridine (3.6 g) and $Et_3N$ (37 ml) at room temperature, and the mixture was stirred at room temperature for 3 days. The obtained reaction mixture was concentrated under reduced pressure to about half volume, methyl-tert-butyl ether and a saturated aqueous sodium hydrogen carbonate solution were added thereto and the aqueous layer was separated. The obtained aqueous layer was washed three times with methyl-tert-butyl ether, 1 M hydrochloric acid was then added thereto to adjust pH to about 2. The acidified aqueous layer was then extracted four times with AcOEt. The obtained organic layers were combined, washed with a saturated aqueous sodium chloride solution, dried over anhydrous sodium sulfate, and subsequently the solvent was distilled off under reduced pressure to give (3R)-3-[(tert-butoxycarbonyl)amino]-2-hydroxy-4-(methylsulfanyl)butanoic acid (13.4 g) as an oily product.

Production Example 15

A mixture of (3R)-3-[(tert-butoxycarbonyl)amino]-2-hydroxy-4-(methylsulfanyl)butanoic acid (16.2 g), 1,2-dichloroethane (186 ml), 2,2-dimethoxypropane (82.2 ml) and pyridinium p-toluenesulfonate (770 mg) was stirred at 80° C. for 15 hours. The obtained reaction mixture was allowed to cool to room temperature, subsequently 2.5% aqueous sodium hydrogen carbonate solution (50 ml) was added thereto and stirred, and subsequently the organic layer was separated. The aqueous layer was extracted with $CHCl_3$, the obtained organic layers were combined, and subsequently washed with a saturated aqueous sodium chloride solution. The obtained organic layer was dried over anhydrous sodium sulfate and concentrated under reduced pressure. The obtained residue was purified by silica gel column chromatography (hexane/AcOEt) to give tert-butyl [(1R)-1-(2,2-dimethyl-5-oxo-1,3-dioxolan-4-yl)-2-(methylsulfanyl)ethyl]carbamate (12.2 g) as an oily product.

Production Example 16

Under nitrogen atmosphere, to a mixture of N-(tert-butoxycarbonyl)-L-serine (20 g) and DMF (480 ml) was added NaH (60% mineral oil dispersion, 8.6 g) in five portions while maintaining an internal temperature below 5° C. under ice-bath cooling and subsequently the mixture was stirred for 1 hour under ice-bath cooling. (2-Iodoethyl)cyclopropane (24 g) was added to the resulting reaction mixture and the mixture was stirred at room temperature for 14 hours. After cooling the resulting reaction mixture with an ice-water bath, water and 1 M hydrochloric acid were added to adjust pH to 2 to 3. The resulting reaction mixture was extracted three times with AcOEt and subsequently the organic layer was washed with a saturated aqueous sodium chloride solution. The obtained organic layer was dried over anhydrous sodium sulfate and concentrated under reduced pressure. MeOH (140 ml) and $CH_2Cl_2$ (420 ml) were added to the resulting residue and then the residue was cooled with an ice-water bath, (diazomethyl)(trimethyl)silane (2 M hexane solution, 62 ml) was added dropwise under ice-bath cooling while maintaining an internal temperature below 6° C. and subsequently the mixture was stirred for 10 minutes under ice-bath cooling and at room temperature for 1 hour. AcOH was added to the resulting reaction mixture and subsequently concentrated under reduced pressure. The resulting residue was purified by silica gel column chromatography (hexane/AcOEt) to give methyl N-(tert-butoxycarbonyl)-O-(2-cyclopropylethyl)-L-serinate (6.51 g) as an oily product.

Production Example 17

Under nitrogen atmosphere, $PBr_3$ (0.58 ml) was added dropwise to a solution of [2-(2-cyclopropylethyl)furo[3,2-c]pyridin-4-yl]methanol (1.33 g) in THF (42 ml) at room temperature. The reaction mixture was stirred at room temperature for 1 hour and subsequently added to a mixture of a saturated aqueous sodium hydrogen carbonate solution and $CH_2Cl_2$ under ice-water bath cooling. The obtained mixture was stirred for 30 minutes, subsequently the organic layer was separated, and the aqueous layer was extracted with $CH_2Cl_2$. The obtained organic layers were combined and washed with a saturated aqueous sodium chloride solution, subsequently dried over anhydrous magnesium sulfate, diluted with toluene and concentrated to about 2 ml under reduced pressure (Mixture A). Under nitrogen atmosphere, a solution of tert-butyl [(1R)-1-(2,2-dimethyl-5-oxo-1,3-dioxolan-4-yl]-2-(methylsulfanyl)ethyl]carbamate (1.7 g) in THF (34 ml) was cooled with a dry ice-acetone bath and LDA (1.09 M hexane-THF solution, 12 ml) was added dropwise thereto. The resulting reaction mixture was stirred for 30 minutes with dry ice-acetone bath cooling. The mixture A was then added dropwise thereto and the mixture was further stirred for 2 hours. A saturated aqueous ammonium chloride solution was added to the obtained mixture, and the mixture was allowed to warm up to room temperature. The obtained mixture was extracted with $CHCl_3$, dried over anhydrous sodium sulfate, and concentrated under reduced pressure. The obtained residue was purified by silica gel column chromatography (hexane/AcOEt) to give tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (923 mg) as an oily product.

Production Example 18

Under nitrogen atmosphere, 2,2,6,6-tetramethylpiperidinyl-magnesium chloride-lithium chloride complex (1M THF-toluene solution, 91 ml) was added dropwise at −20° C. over 2 hours to a mixture of methyl N-(tert-butoxycarbonyl)-O-(2-cyclopropylethyl)-L-serinate (6.5 g), dibromomethane (8.0 g) and THF (22 ml) while maintaining an internal temperature bellow −11° C. and subsequently stirred at −15° C. for 2 hours. The reaction mixture was poured into a mixture of 5% aqueous citric acid solution and AcOEt (cooled with ice-water bath) and subsequently stirred for 10 minutes. The organic layer was separated, and washed with 5% aqueous citric acid solution three times and subsequently a saturated aqueous sodium chloride solution. The obtained organic layer was dried over anhydrous sodium sulfate, and subsequently concentrated under reduced pressure to give the residue (10.7 g) containing tert-butyl [(2S)-4,4-dibromo-1-(2-cyclopropylethoxy)-3-oxobutan-2-yl]carbamate as an oily product.

Production Example 19

2 M Aqueous sodium hydroxide solution (57 ml) was added dropwise under ice-bath cooling to a mixture of tert-butyl [(2S)-4,4-dibromo-1-(2-cyclopropylethoxy)-3-oxobutan-2-yl]carbamate (9.6 g) and toluene (76 ml) over 15 minutes and the mixture was subsequently stirred at room temperature for 2 hours. Toluene and water were added to the resulting reaction mixture and subsequently the organic layer and the aqueous layer were separated. The organic layer was extracted twice with water, and the obtained water layer was combined with the previously obtained aqueous layer, and subsequently AcOEt was added thereto. After cooling the obtained mixture with an ice-water bath, 2 M hydrochloric acid was added to adjust pH of the aqueous layer to about 1.5. The organic layer and the aqueous layer of the resulting reaction mixture were separated and the aqueous layer was extracted three times with AcOEt. The obtained organic layers were combined and dried over anhydrous sodium sulfate. The obtained organic layer was concentrated under reduced pressure to give (3S)-3-[(tert-butoxycarbonyl)amino]-4-(2-cyclopropylethoxy)-2-hydroxybutanoic acid (4.53 g) as an oily product.

Production Example 20

Sodium methoxide (28% MeOH solution, 0.2 ml) was added to a mixture of 2-ethylhexyl 3-{[2-cyano-3-(hex-1- yn-1-yl)pyridin-4-yl]sulfanyl}propanoate (271 mg) and MeOH (5.5 ml) at room temperature, and the mixture was stirred at 40° C. for 2 hours, subsequently sodium methoxide (28% MeOH solution, 0.14 ml) was added thereto, and the mixture was further stirred at the same temperature for 1.5 hours. 3 M Hydrochloric acid (0.8 ml) was added to the obtained reaction mixture under ice-bath cooling and the mixture was stirred at room temperature for 2.5 hours. The obtained reaction mixture was concentrated under reduced pressure, a saturated aqueous sodium hydrogen carbonate solution was added to the residue and the mixture was extracted three times with AcOEt. The obtained organic layer was dried over anhydrous magnesium sulfate and concentrated under reduced pressure. The obtained residue was purified by silica gel column chromatography (hexane/AcOEt) to give 2-butylthieno[3,2-c]pyridin-4-methyl carboxylate (107 mg) as an oily product.

Production Example 21

A mixture of tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (105 mg) and CH$_2$Cl$_2$ (2 ml) was cooled with an ice-water bath, subsequently m-chloroperbenzoic acid (contains ca. 25% water, 48 mg) was added thereto and the mixture was stirred at the same temperature for 1 hour. 10% Aqueous sodium thiosulfate solution was added to the resulting reaction mixture under ice-bath cooling and the mixture was stirred for 10 minutes. After separating the aqueous layer and the organic layer, the organic layer was washed twice with a saturated aqueous sodium hydrogen carbonate solution. The obtained organic layer was dried over anhydrous magnesium sulfate and subsequently concentrated under reduced pressure. The resulting residue was purified by silica gel column chromatography (CHCl$_3$/MeOH) to give tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methyl sulfinyl)ethyl]carbamate (85 mg) as a foamy solid.

Production Example 22

A mixture of tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (121 mg) and CH$_2$Cl$_2$ (7 ml) was cooled with an ice-water bath, subsequently m-chloroperbenzoic acid (contains ca. 25% water, 111 mg) was added thereto and the mixture was stirred at room temperature for 1 hour. The resulting reaction mixture was cooled again with an ice-water bath, m-chloroperbenzoic acid (contains ca. 25% water, 11 mg) was added thereto and the mixture was stirred at room temperature for 30 minutes. 10% Aqueous sodium thiosulfate solution was added to the resulting reaction mixture under ice-bath cooling and the mixture was stirred for 10 minutes. After separating the aqueous layer and the organic layer, the organic layer was washed twice with a saturated aqueous sodium hydrogen carbonate solution. The obtained organic layer was dried over anhydrous magnesium sulfate and subsequently concentrated under reduced pressure. The resulting residue was purified by silica gel column chromatography (CHCl$_3$/AcOEt) to give tert-butyl [(1R)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfonyl) ethyl]carbamate (83 mg) as a foamy solid.

Production Example 23

After cooling a mixture of (3R,4S)-3-{[2-(2-cyclopropylethyl)furo[3,2-c]pyridin-4-yl]methyl}-3-(methoxymethoxy)-1-(methoxymethyl)-4-{[(triisopropylsilyl)oxy]methyl}azetidin-2-one (1.6 g) and THF (30 ml) with an ice-water bath, tetra-n-butylammonium fluoride (1 M THF solution, 3 ml) was added thereto and the mixture was stirred at the same temperature for 1 hour. A saturated aqueous ammonium chloride solution was added to the reaction mixture and the mixture was extracted twice with AcOEt. The organic layer was washed with a saturated aqueous sodium chloride solution, dried over anhydrous magnesium sulfate and subsequently concentrated under reduced pressure. The resulting residue was purified by silica gel column chromatography (CHCl$_3$/MeOH) to give (3R,4S)-3-{[2-(2-cyclopropylethyl)furo[3,2-c]pyridin-4-yl]methyl}-4-(hydroxymethyl)-3-(methoxymethoxy)-1-(methoxymethyl)azetidin-2-one (937 mg) as an oily product.

Production Example 24

Methanesulfonyl chloride (0.37 ml) was added at room temperature to a mixture of (3R,4S)-3-{[2-(2-cyclopropylethyl)furo[3,2-c]pyridin-4-yl]methyl}-4-(hydroxymethyl)-3-(methoxymethoxy)-1-(methoxymethyl)azetidin-2-one (936 mg), pyridine (0.75 ml) and CH$_2$Cl$_2$ (10 ml) and the mixture was stirred at the same temperature for 15 hours. CHCl$_3$ was added to the resulting reaction mixture and washed sequentially with 0.5 M hydrochloric acid, a saturated aqueous sodium hydrogen carbonate solution and a saturated aqueous sodium chloride solution. The obtained organic layer was dried over anhydrous magnesium sulfate and concentrated under reduced pressure. The resulting residue was purified by silica gel column chromatography (hexane/AcOEt) to give [(2S,3R)-3-{[2-(2-cyclopropylethyl)furo[3,2-c]pyridin-4-yl]methyl}-3-(methoxymethoxy)-1-(methoxymethyl)-4-oxoazetidin-2-yl] methyl methanesulfonate (1.11 g) as an oily product.

Production Example 25

A mixture of [(2S,3R)-3-{[2-(2-cyclopropylethyl)furo[3,2-c]pyridin-4-yl]methyl}-3-(methoxymethoxy)-1-(methoxymethyl)-4-oxoazetidin-2-yl]methyl methanesulfonate (1.11 g), DMF (20 ml) and potassium thioacetate (400 mg) was stirred at 60° C. for 7 hours. Potassium thioacetate (53 mg) was added to the obtained reaction mixture at room temperature and the mixture was further stirred at 60° C. for 12 hours. After addition of AcOEt, the obtained mixture was washed sequentially with water, a saturated aqueous sodium hydrogen carbonate solution and a saturated aqueous sodium chloride solution, and dried over anhydrous magnesium sulfate. The obtained organic layer was concentrated under reduced pressure to give S-{[(2R,3R)-3-{[2-(2-cyclopropylethyl)furo[3,2-c]pyridin-4-yl]methyl}-3-(methoxymethoxy)-1-(methoxymethyl)-4-oxoazetidin-2-yl]methyl} thioacetate (1.02 g) as an oily product.

Production Example 26

Under nitrogen atmosphere, potassium carbonate (50 mg) was added to a mixture of S-{[(2R,3R)-3-{[2-(2-cyclopropylethyl)furo[3,2-c]pyridin-4-yl]methyl}-3-(methoxymethoxy)-1-(methoxymethyl)-4-oxoazetidin-2-yl] methyl} thioacetate (80 mg), iodoethane (0.03 ml), DMF (0.8 ml) and MeOH (0.8 ml), and the mixture was stirred at room temperature for 16 hours. After addition of AcOEt, the obtained mixture was washed sequentially with water, a saturated aqueous sodium hydrogen carbonate solution and a saturated aqueous sodium chloride solution, and dried over anhydrous magnesium sulfate. The obtained organic layer was concentrated under reduced pressure to give (3R,4R)-3-{[2-(2-cyclopropylethyl)furo[3,2-c]pyridin-4-yl]methyl}-4-[(ethylsulfanyl)methyl]-3-(methoxymethoxy)-1-(methoxymethyl)azetidin-2-one (67 mg) as an oily product.

Production Example 27

Under nitrogen atmosphere, a mixture of trimethylsilylacetylene (25 ml) and THF (170 ml) was cooled to −78° C. and n-butyl lithium (1.6 M hexane solution, 115 ml) was added dropwise. The resulting reaction mixture was stirred for 15 minutes under ice-bath cooling and subsequently cooled again to −78° C. N,N,N',N',N'',N''-Hexamethylphosphoric acid triamide (32 ml) was added to the resulting reaction mixture, and the mixture was stirred at the same temperature for 30 minutes, subsequently (2-bromoethyl)cyclopropane (27 g) was added dropwise thereto over 5 minutes and the mixture was stirred at the same temperature for 30 minutes. The resulting reaction mixture was allowed to warm up to room temperature and stirred for 16 hours. Water was added to the resulting reaction mixture under ice-bath cooling and the organic layer was separated. The obtained organic layer was washed with a saturated aqueous sodium chloride solution, dried over anhydrous magnesium sulfate and subsequently concentrated under reduced pressure to give (4-cyclopropylbut-1-yn-1-yl)(trimethyl)silane (31.8 g) as an oily product.

Production Example 28

Under argon atmosphere, tetra-n-butylammonium fluoride (1 M THF solution, 8.8 ml) was added to a mixture of 3-bromopyridin-4(1H)-one (500 mg), (4-cyclopropylbut-1-yn-1-yl)(trimethyl)silane (1.44 g), Et$_3$N (2.8 ml) and DMF (5 ml). The obtained mixture was subjected to an ultrasonication for 30 seconds, subsequently bis(triphenylphosphine)palladium (II) dichloride (420 mg) was added thereto and the mixture was stirred at 110° C. for 1 hour under microwave irradiation. AcOEt and silica gel were added to the resulting reaction mixture and the mixture was concentrated under reduced pressure. The resulting residue was purified by silica gel column chromatography (hexane/AcOEt) to give 2-(2-cyclopropylethyl)furo[3,2-c]pyridine (302 mg) as an oily product.

Production Example 29

Under nitrogen atmosphere, m-chloroperbenzoic acid (contains ca. 25% water, 555 mg) was added under ice-bath cooling to a mixture of 2-(2-cyclopropylethyl)furo[3,2-c]pyridine (300 mg) and CHCl$_3$ (6 ml). After stirring the resulting reaction mixture at room temperature for 8 hours, the mixture was cooled with an ice-water bath and m-chloroperbenzoic acid (contains ca. 25% water, 300 mg) was added again thereto. The resulting reaction mixture was further stirred at room temperature for 16 hours. After cooling the resulting reaction mixture with an ice-water bath, a saturated aqueous sodium hydrogen carbonate solution and 5% aqueous sodium sulfite solution were added thereto and the mixture was extracted three times with CHCl$_3$. The obtained organic layer was dried over anhydrous sodium sulfate and subsequently concentrated under reduced pressure. The resulting residue was purified by silica gel column chromatography (CHCl$_3$/MeOH) to give 2-(2-cyclopropylethyl)furo[3,2-c]pyridine 5-oxide (190 mg) as an oily product.

Production Example 30

Under nitrogen atmosphere, trimethylsilylcyanide (0.183 ml) was added to a mixture of 2-(2-cyclopropylethyl)furo[3,2-c]pyridine 5-oxide (190 mg), Et$_3$N (0.33 ml) and MeCN (4 ml) and the mixture was stirred at 85° C. for 16 hours. After cooling the resulting reaction mixture to room temperature, Et$_3$N (0.65 ml) and trimethylsilylcyanide (0.35 ml) were added thereto. The reaction mixture was stirred again at 85° C. for 3.5 hours, subsequently AcOEt was added to the resulting reaction mixture, and the mixture was washed sequentially with a saturated aqueous sodium hydrogen carbonate solution and a saturated aqueous sodium chloride solution. The obtained organic layer was dried over anhydrous magnesium sulfate and concentrated under reduced pressure. The resulting residue was purified by silica gel column chromatography (hexane/AcOEt) to give 2-(2-cyclopropylethyl)furo[3,2-c]pyridine-4-carbonitrile (148 mg) as an oily product.

Production Example 31

Sodium methoxide (a 28% MeOH solution, 0.14 ml) was added to a mixture of 2-(2-cyclopropylethyl)furo[3,2-c]pyridine-4-carbonitrile (148 mg) and MeOH (1.5 ml) under ice-bath cooling, and the mixture was stirred at room temperature for 1.5 hours. 3 M Hydrochloric acid (0.7 ml) was added to the obtained reaction mixture under ice-bath cooling and the mixture was stirred at room temperature for 18 hours. Water and MeOH were added to the obtained reaction mixture, and the mixture was concentrated under reduced pressure. A saturated aqueous sodium hydrogen carbonate solution was added to the obtained residue and the mixture was extracted twice with AcOEt. The obtained organic layer was washed with a saturated aqueous sodium chloride solution, dried over anhydrous magnesium sulfate and the organic layer was concentrated under reduced pressure. Under nitrogen atmosphere, to a mixture of the resulting residue and MeOH (4 ml) was added NaBH$_4$ (80 mg) under ice-bath cooling, and the mixture was gradually allowed to warm up to room temperature with stirring over 1 hour, and then stirred for 5 hours. The resulting reaction mixture was cooled again with an ice-water bath, subsequently NaBH$_4$ (80 mg) was added thereto, and the mixture was gradually allowed to warm up to room temperature with stirring over 1 hour, and then stirred for 15 hours. Acetone was added to the obtained reaction mixture at room temperature and subsequently the mixture was concentrated under reduced pressure. Water was added to the obtained residue and the mixture was extracted three times with AcOEt. The obtained organic layer was dried over anhydrous magnesium sulfate and concentrated under reduced pressure. The resulting residue was purified by silica gel column chromatography (eluted with hexane/AcOEt and subsequently with CHCl$_3$/MeOH) to give [2-(2-cyclopropylethyl)furo[3,2-c]pyridin-4-yl]methanol (123 mg) as an oily product.

Production Example 32

Under nitrogen atmosphere, N,N-dimethylcarbamoyl chloride (12.5 ml) was added to a mixture of 4-chloro-3-iodopyridine 1-oxide (21 g) and 1,2-dichloroethane (230 ml), and the mixture was stirred at room temperature for 30 minutes. Trimethylsilylcyanide (20.5 ml) was added to the obtained reaction mixture and the mixture was stirred at 60° C. for 6 hours. The obtained reaction mixture was allowed to cool to room temperature, subsequently a saturated aqueous sodium hydrogen carbonate solution (260 ml) was added thereto and the mixture was stirred for 30 minutes. The obtained reaction mixture was extracted twice with AcOEt, the organic layer was washed with a saturated aqueous sodium chloride solution and dried over anhydrous magnesium sulfate. The obtained organic layer was concentrated under reduced pressure, the residue was washed with a mixture of hexane and isopropanol to give 4-chloro-3-iodopyridine-2-carbonitrile (7.1 g) as a solid.

Production Example 33

Cesium acetate (30 g) was added to a mixture of 4-chloro-3-iodopyridine-2-carbonitrile (8.4 g) and DMF (170 ml), and the mixture was stirred at 100° C. overnight. 1 M Hydrochloric acid (191 ml) was added to the obtained reaction mixture under ice-bath cooling, and the mixture was extracted twice with AcOEt. The obtained organic layer was washed twice with 5% aqueous sodium chloride solution and dried over anhydrous magnesium sulfate. The obtained organic layer was concentrated under reduced pressure followed by co-evaporation with toluene for three times. To the obtained residue was added diisopropyl ether, and the resulting insoluble materials were collected by filtration. The obtained solid was washed with a mixture of diisopropyl ether and isopropanol to give 4-hydroxy-3-iodopyridine-2-carbonitrile (4.4 g) as a solid.

Production Example 34

2-Ethylhexyl 3-sulfanylpropanoate (1.73 ml) was added to a mixture of 4-chloro-3-iodopyridine-2-carbonitrile (1.82 g), Et$_3$N (1.92 ml) and DMF (18 ml) under ice-bath cooling and subsequently the mixture was stirred at room temperature for 18 hours. AcOEt and water were added to the obtained reaction mixture and the organic layer was separated. The obtained organic layer was washed with a saturated aqueous sodium chloride solution and dried over anhydrous magnesium sulfate. The obtained organic layer was concentrated under reduced pressure and the residue was purified by silica gel column chromatography (hexane/AcOEt) to give 2-ethylhexyl 3-[(2-cyano-3-iodopyridin-4-yl)sulfanyl]propanoate (254 mg) as an oily product.

Production Example 35

Under nitrogen atmosphere, bis(triphenylphosphine)palladium (II) dichloride (79 mg) was added to a mixture of 2-ethylhexyl 3-[(2-cyano-3-iodopyridin-4-yl)sulfanyl]propanoate (252 mg), 1-hexyne (0.128 ml), Et$_3$N (0.394 ml) and MeCN (5 ml), and the mixture was stirred at 70° C. for 3.5 hours. The obtained reaction mixture was allowed to cool to room temperature and subsequently concentrated under reduced pressure. The resulting residue was purified by silica gel column chromatography (hexane/AcOEt) to give 2-ethylhexyl 3-{[2-cyano-3-(hexa-1-yn-1-yl)pyridin-4-yl]sulfanyl}propanoate (178 mg) as an oily product.

Production Example 36

Under nitrogen atmosphere, NaBH$_4$ (102 mg) was added under ice-bath cooling to a mixture of 2-butylthieno[3,2-c]pyridine-4-methyl carboxylate (112 mg) and MeOH (3.4 ml), and the mixture was gradually allowed to warm up to room temperature with stirring over 1 hour, and then stirred for 12 hours. Acetone was added to the obtained reaction mixture at room temperature and subsequently the mixture was concentrated under reduced pressure. Water was added to the obtained residue and the mixture was extracted three times with AcOEt. The obtained organic layer was dried over anhydrous magnesium sulfate and concentrated under reduced pressure. The obtained residue was purified by silica gel column chromatography (CHCl$_3$/MeOH) to give (2-butylthieno[3,2-c]pyridin-4-yl)methanol (95 mg) as an oily product.

Production Example 37

Under nitrogen atmosphere, a solution of thionyl chloride (0.075 ml) in CH$_2$Cl$_2$ (0.6 ml) was added to a mixture of (2-butylthieno[3,2-c]pyridin-4-yl)methanol (113 mg) and CH$_2$Cl$_2$ (1.2 ml) under ice-bath cooling. The obtained reaction mixture was stirred at room temperature for 1 hour. The obtained reaction mixture was concentrated under reduced pressure to give 2-butyl-4-(chloromethyl)thieno[3,2-c]pyridine hydrochloride (140 mg) as a solid.

Production Example 38

Under nitrogen atmosphere, sodium iodide (225 mg) was added to a mixture of 2-butyl-4-(chloromethyl)thieno[3,2-c]pyridine hydrochloride (139 mg) and CH$_2$Cl$_2$ (5.6 ml), and the mixture was stirred at room temperature for 30 minutes. A saturated aqueous sodium hydrogen carbonate solution was added to the obtained reaction mixture, the mixture was stirred for 5 minutes, and subsequently extracted twice with CH$_2$Cl$_2$. The obtained organic layer was dried over anhydrous magnesium sulfate and then diluted with toluene. The obtained mixture was concentrated under reduced pressure to about 5 ml. The procedure, in which toluene was added again to the obtained mixture and the mixture was concentrated under reduced pressure to about 3 ml, was repeated twice (Mixture A).

Under nitrogen atmosphere, LDA (1.13M hexane-THF solution, 1 ml) was added dropwise with stirring at −78° C. to a mixture of tert-butyl [(1R)-1-(2,2-dimethyl-5-oxo-1,3-dioxolan-4-yl)-2-(methylsulfanyl)ethyl]carbamate (143 mg) and THF (2.8 ml). After stirring the obtained reaction mixture at the same temperature for 30 minutes, the mixture A was added dropwise thereto. After stirring the obtained reaction mixture at the same temperature for 1 hour, a saturated aqueous ammonium chloride solution was added, and allowed to warm up to room temperature. The obtained mixture was extracted twice with AcOEt and the organic layer was dried over anhydrous magnesium sulfate. The obtained organic layer was concentrated under reduced pressure and the residue was purified by silica gel column chromatography (hexane/AcOEt) to give tert-butyl [(1R)-1-{(4R)-4-[(2-butylthieno[3,2-c]pyridin-4-yl]methyl]-2,2-dimethyl-5-oxo-1,3-dioxolan-4-yl}-2-(methylsulfanyl)ethyl]carbamate (170 mg) as an oily product.

Production Example 39

Under nitrogen atmosphere, CuI (93 mg) and bis(triphenylphosphine)palladium (II) dichloride (58 mg) were added to a mixture of 4-hydroxy-3-iodopyridine-2-carbonitrile (400 mg), ethynylcyclopentane (0.205 ml), Et$_3$N (0.91 ml) and MeCN (8 ml), and the mixture was stirred at 70° C.

overnight. The obtained reaction mixture was allowed to cool to room temperature and subsequently concentrated under reduced pressure. The resulting residue was purified by silica gel column chromatography (hexane/AcOEt) to give 2-cyclopentylfuro[3,2-c]pyridine-4-carbonitrile (270 mg) as an oily product.

Production Example 40

10% Pd/C (contains ca. 50% water, 200 mg) was added to a mixture of tert-butyl [(1R)-1-[(4R)-4-{[2-(2-cyclopropyl-ethyl)furo[3,2-c]pyridin-4-yl]methyl}-2,2-dimethyl-5-oxo-1,3-dioxolan-4-yl]-2-(methylsulfanyl)ethyl]carbamate (200 mg), AcOH (2 mL) and EtOH (2 mL), and the mixture was stirred at room temperature for 5 days under hydrogen atmosphere of 3.5 atm. Celite was added to the resulting reaction mixture, and the insoluble materials were removed by filtration. The filtrate was concentrated under reduced pressure and the obtained residue was purified by silica gel column chromatography (hexane/AcOEt) to give tert-butyl [(1R)-1-[(4R)-4-{[2-(2-cyclopropylethyl)-2,3-dihydrofuro[3,2-c]pyridin-4-yl]methyl}-2,2-dimethy-5-oxo-1,3-dioxo-lane-4-yl]-2-(methylsulfanyl)ethyl]carbamate (58 mg) as an oily product.

Production Example 41

Under nitrogen atmosphere, bis(triphenylphosphine)palladium (II) dichloride (230 mg) was added to a mixture of 4-hydroxy-3-iodopyridine-2-carbonitrile (800 mg), 3-hexyne (1.12 ml), Et₃N (1.82 ml) and DMF (16 ml), and the mixture was stirred at 150° C. for 2 hours under microwave irradiation. Water was added to the obtained reaction mixture and the mixture was extracted with AcOEt. The organic layer was concentrated under reduced pressure and the residue was purified by silica gel column chromatography (hexane/AcOEt) to give 2,3-diethylfuro[3,2-c]pyridine-4-carbonitrile (215 mg) as an oily product.

Production Example 42

Sodium methoxide (28% MeOH solution, 0.29 ml) was added to a mixture of 2,3-diethylfuro[3,2-c]pyridine-4-carbonitrile (240 mg) and MeOH (3 ml) and the mixture was stirred at 40° C. overnight. Sodium methoxide (28% MeOH solution, 0.29 ml) was added again to the obtained reaction mixture and the mixture was stirred at 60° C. for 3 hours. 6 M aqueous sodium hydroxide solution (3 ml) and EtOH (3 ml) were added to the obtained reaction mixture and the mixture was stirred at 80° C. overnight. 6 M Hydrochloric acid (3.5 ml) was added to the obtained reaction mixture under ice-bath cooling to neutralize the mixture, water was added thereto, and the mixture was extracted twice with CHCl₃. The obtained organic layer was dried over anhydrous magnesium sulfate to give 2,3-diethylfuro[3,2-c]pyridine-4-carboxylic acid (150 mg) as an oily product.

Production Example 43

Under nitrogen atmosphere, isobutyl chloroformate (0.1 ml) and N-methylmorpholine (0.09 ml) were added to a mixture of 2,3-diethylfuro[3,2-c]pyridine-4-carboxylic acid (140 mg) and THF (1.5 ml) under ice-bath cooling, and the mixture was stirred at the same temperature for 30 minutes. Insoluble materials were removed from the resulting reaction mixture by filtration, the obtained filtrate was added to a mixture of NaBH₄ (105 mg) and water (1.5 ml) under ice-bath cooling, and the mixture was stirred at room temperature for 2 hours. The obtained reaction mixture was cooled with an ice-water bath, acetone (0.2 ml) was added thereto, and the mixture was extracted with AcOEt. The obtained organic layer was washed with a saturated aqueous sodium chloride solution and dried over anhydrous magnesium sulfate. The obtained organic layer was concentrated under reduced pressure and the residue was purified by silica gel column chromatography (hexane/AcOEt) to give (2,3-diethylfuro[3,2-c]pyridin-4-yl)methanol (70 mg) as an oily product.

Production Example 44

Sodium iodide (155 mg) was added to a mixture of 4-(chloromethyl)-2,3-diethylfuro[3,2-c]pyridine hydrochloride (73 mg) and CH₂Cl₂ (1.4 ml), and the mixture was stirred at room temperature for 1 hour. A saturated aqueous sodium hydrogen carbonate solution was added to the obtained reaction mixture, the mixture was stirred for 5 minutes, and subsequently extracted with toluene. The obtained organic layer was washed with a saturated aqueous sodium chloride solution, dried over anhydrous magnesium sulfate and evaporated under reduced pressure. The obtained residue was co-evaporated twice with toluene and then toluene (1 ml) was added to give a solution (Mixture A).

Under argon atmosphere, LDA (1.13 M hexane-THF solution, 0.3 ml) was added dropwise at −78° C. with stirring to a mixture of (3R,4R)-4-[(ethylsulfanyl)methyl]-3-(methoxymethoxy)-1-(methoxymethyl)azetidin-2-one (70 mg) and THF (2.8 ml). After stirring the obtained reaction mixture at the same temperature for 20 minutes, the mixture A was added dropwise thereto. After stirring the obtained reaction mixture at the same temperature for 2 hours, AcOH (0.025 ml) was added thereto and the mixture was allowed to warm up to room temperature. Water was added to the obtained mixture and the mixture was extracted with CHCl₃. The obtained organic layer was washed with a saturated aqueous sodium chloride solution and dried over anhydrous magnesium sulfate. The obtained organic layer was concentrated under reduced pressure and the residue was purified by silica gel column chromatography (hexane/AcOEt) to give (3R,4R)-3-[(2,3-diethylfuro[3,2-c]pyridin-4-yl)methyl]-4-[(ethylsulfanyl)methyl]-3-(methoxymethoxy)-1-(methoxymethyl)azetidin-2-one (95 mg) as an oily product.

Production Example 45

Sodium ethanethiolate (505 mg) was added under ice-bath cooling to a solution of [(2S,3R)-3-(methoxymethoxy)-1-(methoxymethyl)-4-oxoazetidin-2-yl]methyl methanesulfonate (900 mg) in DMF (9 ml) and the mixture was stirred at the same temperature for 1 hour. After addition of AcOEt, the obtained mixture was washed sequentially with water, a saturated aqueous sodium hydrogen carbonate solution and a saturated aqueous sodium chloride solution, and dried over anhydrous magnesium sulfate. The obtained organic layer was concentrated under reduced pressure and the residue was purified by silica gel column chromatography (hexane/AcOEt) to give (3R,4R)-4-[(ethyl sulfanyl)methyl]-3-(methoxymethoxy)-1-(methoxymethyl)azetidin-2-one (557 mg) as an oily product.

Production Example 46

Under nitrogen atmosphere, urea hydrogen peroxide (2.46 g) and methyltrioxorhenium (VII) (85.7 mg) were added under ice-bath cooling to a mixture of 2-butyl-7-methylfuro[3,2-c]pyridine (3.3 g) and CHCl₃ (40 ml). After stirring the obtained reaction mixture at room temperature for 30 minutes, the mixture was cooled again with an ice-water bath, urea hydrogen peroxide (2.47 g) and methyltrioxorhenium (VII) (131 mg) were added thereto. After stirring the obtained reaction mixture at room temperature for 1 hour, manganese dioxide (150 mg) was added thereto, and the mixture was further stirred for 1.5 hours. Insoluble materials were removed by filtration and washed with CHCl₃-MeOH (98:2). 5% Aqueous sodium sulfite solution was added to the obtained filtrate and the resulting mixture was extracted three times with CHCl₃-MeOH (98:2). The obtained organic layer was dried over anhydrous magnesium sulfate and concentrated under reduced pressure to give 2-butyl-7-methylfuro[3,2-c]pyridine 5-oxide (3.97 g) as a solid.

Production Example 47

Under nitrogen atmosphere, potassium carbonate (50 mg) was added to a mixture of S-{[(2R,3R)-3-{[2-(2-cyclopropylethyl)furo[3,2-c]pyridin-4-yl]methyl}-3-(methoxymethoxy)-1-(methoxymethyl)-4-oxoazetidin-2-yl]methyl}thioacetate (80 mg), (bromomethyl)cyclopropane (0.035 ml), sodium iodide (52 mg), DMF (0.8 ml) and MeOH (0.8 ml), and the mixture was stirred at room temperature for 4 hours. After addition of AcOEt, the obtained mixture was washed sequentially with water, a saturated aqueous sodium hydrogen carbonate solution and a saturated aqueous sodium chloride solution. The obtained organic layer was dried over anhydrous magnesium sulfate and concentrated under reduced pressure to give (3R,4R)-3-{[2-(2-cyclopropylethyl)furo[3,2-c]pyridin-4-yl]methyl}-4-{[(cyclopropylmethyl)sulfanyl]methyl}-3-(methoxymethoxy)-1-(methoxymethyl)azetidin-2-one (73 mg) as an oily product.

Production Example 48

Di-tert-butyl dicarbonate (60 ml) was added to a mixture of (3S)-3-amino-2-hydroxy-4-(methylsulfanyl)butanoate hydrochloride (27.7 g), THF (139 ml), water (139 ml) and Et₃N (57.4 ml), and the mixture was stirred at room temperature overnight. N,N-Dimethylethyleneamine (7.5 ml) was added to the obtained reaction mixture and the mixture was stirred at room temperature for 2 hours. 1 M aqueous sodium hydrogensulfate solution (371 ml) was added the obtained reaction mixture, and the aqueous layer and the organic layer were separated. The obtained aqueous layer was extracted three times with AcOEt. The obtained organic layers were combined, washed with a saturated aqueous sodium chloride solution and dried over anhydrous sodium sulfate. The obtained organic layer was concentrated under reduced pressure, AcOEt (416 ml) and dicyclohexylamine (27.3 ml) were added to the residue, and the mixture was stirred at room temperature overnight. The obtained mixture was concentrated under reduced pressure, diisopropyl ether (416 ml) was added to the residue, and the mixture was stirred at room temperature for 1 hour, stirred for 2 hours under ice-bath cooling, and stirred at room temperature overnight. Insoluble material was removed by filtration from the resulting mixture and subsequently the filtrate was concentrated under reduced pressure. Diisopropyl ether (416 ml) was added to the obtained residue, and the mixture was stirred at room temperature for 3 days. The resulting insoluble materials were collected by filtration and dried under reduced pressure. Diisopropyl ether (416 ml) was added again to the obtained solid, and the mixture was stirred at room temperature for 1 hour. The resulting insoluble materials were collected by filtration to give (3S)-3-[(tert-butoxycarbonyl)amino]-2-hydroxy-4-(methylsulfanyl)butanoic acid-dicyclohexylamine (1:1) (30.2 g) as a solid.

Production Example 49

Under argon atmosphere, 2,2-dimethoxypropane (83 ml) and p-toluenesulfonic acid monohydrate (14.1 g) were added to a mixture of (3S)-3-[(tert-butoxycarbonyl)amino]-2-hydroxy-4-(methylsulfanyl)butanoic acid-dicyclohexylamine (1:1) (30.1 g) and AcOEt (301 ml), and the mixture was stirred at 70° C. for 16 hours. The obtained reaction mixture was allowed to cool to room temperature and insoluble materials were removed by filtration. The obtained filtrate was washed sequentially with 2.5% aqueous sodium hydrogen carbonate solution once, 0.5 M hydrochloric acid three times, and 2.5% aqueous sodium hydrogen carbonate solution once. The obtained organic layer was washed with a saturated aqueous sodium chloride solution and dried over anhydrous sodium sulfate. The obtained organic layer was concentrated under reduced pressure, AcOEt (90 ml), hexane (180 ml), silica gel (28 g) and activated charcoal (2.8 g) were added to the residue, and the mixture was stirred at room temperature for 1 hour. Insoluble materials were removed from the obtained mixture by filtration and the obtained filtrate was concentrated under reduced pressure to give tert-butyl [(1S)-1-(2,2-dimethyl-5-oxo-1,3-dioxolan-4-yl)-2-(methylsulfanyl)ethyl]carbamate (12.7 g) as an oily product.

Production Example 50

4-(Chloromethyl)-2-(2-cyclopropylethyl)furo[3,2-c]pyridine hydrochloride (1.76 g) was obtained as a solid from [2-(2-cyclopropylethyl)furo[3,2-c]pyridin-4-yl]methanol (1.41 g) in the same manner as in the method described in Production Example 37. Under nitrogen atmosphere, sodium iodide (810 g) was added to a mixture of the obtained 4-(chloromethyl)-2-(2-cyclopropylethyl)furo[3,2-c]pyridine hydrochloride (668 mg) and CH₂Cl₂ (7.5 ml), and the mixture was stirred at room temperature for 1 hour. A saturated aqueous sodium hydrogen carbonate solution was added to the obtained reaction mixture, the mixture was stirred for 5 minutes, and subsequently extracted twice with toluene. The obtained organic layer was washed with a saturated aqueous sodium chloride solution, dried over anhydrous sodium sulfate and subsequently concentrated under reduced pressure. The procedure, in which toluene was added again to the obtained mixture and, the mixture was concentrated under reduced pressure, was repeated three times to give a final volume of about 5 ml toluene solution. (Mixture A).

Under argon atmosphere, LDA (1.13 M hexane-THF solution, 1.45 ml) was added dropwise at −78° C. with stirring to a mixture of tert-butyl [(1 S)-1-(2,2-dimethyl-5-oxo-1,3-dioxolan-4-yl)-2-methylsulfanyl)ethyl]carbamate (500 mg) and THF (5 ml). After stirring the obtained reaction mixture at the same temperature for 10 minutes, chlorotrimethylsilane (0.207 ml) was added thereto and the mixture was stirred at the same temperature for 30 minutes. The obtained reaction mixture was stirred for 30 minutes under ice-bath cooling, subsequently LDA (1.13 M hexane-THF solution, 1.74 ml) was added dropwise thereto with stirring at −78° C. After stirring the obtained reaction mixture at the same temperature for 30 minutes, the mixture A was added dropwise thereto. After stirring the obtained reaction mixture at the same temperature for 2 hours, AcOH (0.094 ml) was added thereto and the mixture was stirred at the same temperature for 10 minutes. 9.5 M Aqueous dimethylamine solution (0.34 ml) was added to the obtained reaction mixture and the mixture was stirred for 30 minutes under ice-bath cooling. 1 M Hydrochloric acid was added to the obtained reaction mixture to neutralize the mixture, and the mixture was extracted twice with AcOEt.

The obtained organic layer was washed with a saturated aqueous sodium chloride solution and dried over anhydrous sodium sulfate. The obtained organic layer was concentrated under reduced pressure and the residue was purified by silica gel column chromatography (hexane/AcOEt) to give tert-butyl [(1 S)-1-[(4R)-4-{[2-(2-cyclopropylethyl)furo[3,2-c]pyridin-4-yl]methyl}-2,2-dimethyl-5-oxo-1,3-dioxolan-4-yl]-2-(methylsulfanyl)ethyl]carbamate (230 mg) as an oily product.

Production Example compounds shown in Tables to be described later were produced in the same manner as in the method described in any of the above Production Examples. Tables to be described later show the structure, physicochemical data and production method of the Production Example compounds.

TABLE 3

| Ex | Str |
|---|---|
| 1 | (structure) |
| 2 | (structure) |

TABLE 3-continued

| Ex | Str |
|---|---|
| 3 | (structure) |
| 4 | (structure) 2HCl |
| 5 | (structure) 2HCl |
| 6 | (structure) 2HCl |

TABLE 3-continued

| Ex | Str |
|---|---|
| 7(1) #1 | (structure) |
| 7(2) #1 | (structure) 2HCl |

TABLE 4

| Ex | Str |
|---|---|
| 8 | (structure) |
| 9 | (structure) 2HCl |
| 10 | (structure) 2HCl |

TABLE 4-continued

| Ex | Str |
|---|---|
| 11 | (structure) |
| 12 | (structure) |
| 13 | (structure) |
| 14 | (structure) |

TABLE 4-continued
| Ex | Str |
|---|---|
| 15 | 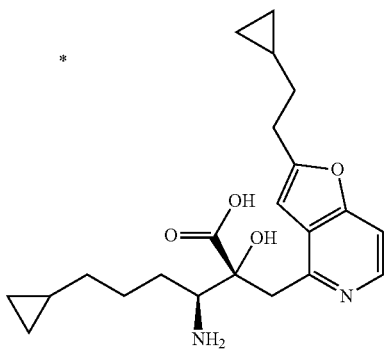 [SMILES: N[C@@H](CCCC1CC1)[C@](O)(Cc1nccc2oc(CCC3CC3)cc12)C(=O)O] |
TABLE 5
| Ex | Str |
|---|---|
| 16 | 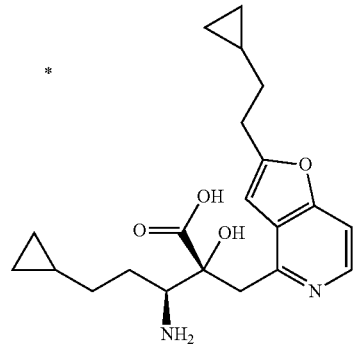 [SMILES: N[C@@H](CCC1CC1)[C@](O)(Cc1nccc2oc(CCC3CC3)cc12)C(=O)O] |
| 17 | 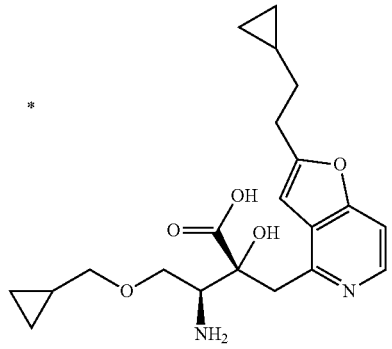 [SMILES: N[C@@H](COCC1CC1)[C@](O)(Cc1nccc2oc(CCC3CC3)cc12)C(=O)O] |
| 18 | 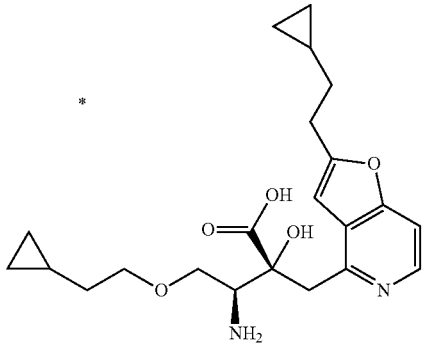 [SMILES: N[C@@H](COCCC1CC1)[C@](O)(Cc1nccc2oc(CCC3CC3)cc12)C(=O)O] |
TABLE 5-continued
| Ex | Str |
|---|---|
| 19 | 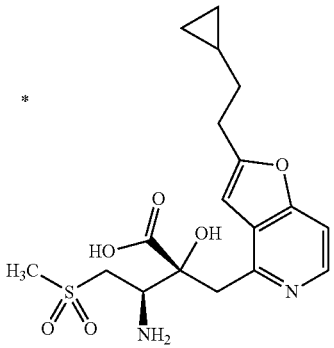 [SMILES: CS(=O)(=O)C[C@H](N)[C@](O)(Cc1nccc2oc(CCC3CC3)cc12)C(=O)O] |
| 20 #2 | 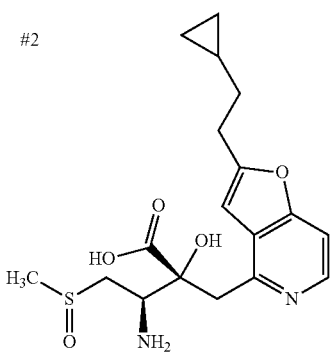 [SMILES: CS(=O)C[C@H](N)[C@](O)(Cc1nccc2oc(CCC3CC3)cc12)C(=O)O] |
| 21 #1 | 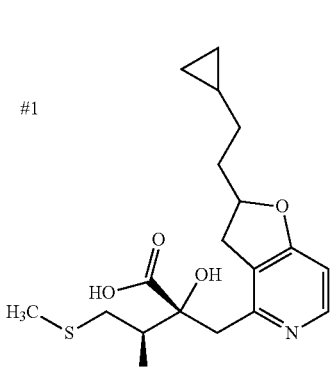 |
| 22 | 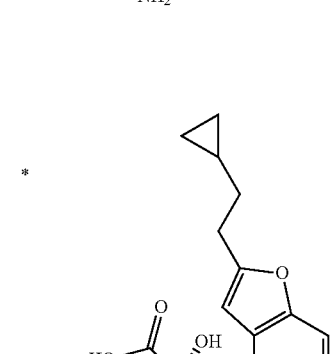 |

TABLE 5-continued

| Ex | Str |
|---|---|
| 23 | 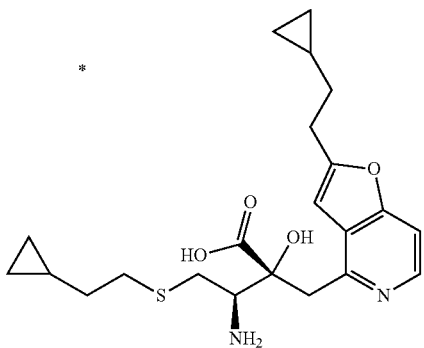 [SMILES: N[C@@H](CSCCC1CC1)[C@](O)(Cc1nccc2oc(CCC3CC3)cc12)C(=O)O] |

TABLE 6

| Ex | Str |
|---|---|
| 24 | |
| 25 | |
| 26 | |

TABLE 6-continued

| Ex | Str |
|---|---|
| 27 | 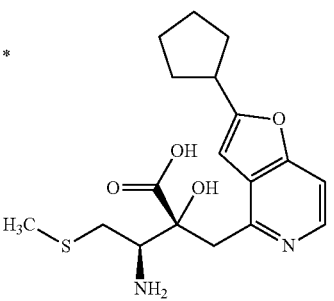 |

TABLE 7

| Ex | Syn | DATA |
|---|---|---|
| 1 | — | ESI+: 379.3<br>$^1$H NMR (400 MHz, MeOH-$d_4$) δ ppm: 0.06-0.10 (2 H, m) 0.43-0.48 (2 H, m) 0.74-0.85 (1 H, m) 1.20 (3 H, t, J = 7.4 Hz) 1.66 (2 H, td, J = 7.4, 7.4 Hz) 2.44-2.55 (3 H, m) 2.92 (2 H, t, J = 7.4 Hz) 3.11 (1 H, dd, J = 11.3, 2.3 Hz) 3.22 (1 H, dd, J = 14.7, 2.5 Hz) 3.45 (2 H, s) 6.74 (1 H, d, J = 1.2 Hz) 7.38 (1 H, dd, J = 5.9, 0.8 Hz) 8.29 (1 H, d, J = 5.9 Hz) |
| 2 | — | ESI+: 365.2<br>$^1$H NMR (500 MHz, MeOH-$d_4$) δ ppm: 0.06-0.11 (2 H, m), 0.43-0.48 (2 H, m), 0.75-0.84 (1 H, m), 1.66 (2 H, td, J = 7.2, 7.2 Hz), 2.03 (3 H, s), 2.54 (1 H, dd, J = 14.4, 11.0 Hz), 2.89-2.94 (2 H, m), 3.09-3.19 (2 H, m), 3.45 (2 H, s), 6.74 (1 H, d, J = 0.8 Hz), 7.38 (1 H, dd, J = 5.7, 0.8 Hz), 8.29 (1 H, d, J = 5.7 Hz) |
| 3 | — | ESI+: 393.2 |
| 4 | — | ESI+: 405.2 |
| 5 | — | ESI+: 379.2 |
| 6 | — | ESI+: 364.2 |
| 7(1) | — | ESI+: 383.1 |
| 7(2) | — | ESI+: 401.1, 403.1 |
| 8 | — | ESI+: 369.1 |
| 9 | — | ESI+: 367.2 |
| 10 | — | ESI+: 367.2 |
| 11 | 1 | ESI+: 419.1 |
| 12 | 1 | ESI+: 405.1 |
| 13 | 1 | ESI+: 393.2 |
| 14 | 1 | ESI+: 387.3 |
| 15 | 1 | ESI+: 387.3 |

TABLE 8

| Ex | Syn | DATA |
|---|---|---|
| 16 | 1 | ESI+: 373.2<br>$^1$H NMR (400 MHz, MeOH-$d_4$): δ ppm −0.02-0.03 (2 H, m), 0.06-0.11 (2 H, m), 0.35-0.41 (2 H, m), 0.43-0.49 (2 H, m), 0.55-0.66 (1 H, m), 0.74-0.85 (1 H, m), 1.15-1.25 (1 H, m), 1.39 (1 H, dddd, J = 13.5, 11.2, 6.7, 4.7 Hz), 1.54-1.63 (1 H, m), 1.66 (2 H, td, J = 7.1, 7.1 Hz), 2.01 (1 H, dddd, J = 14.4, 11.1, 6.3, 3.2 Hz), 2.88-2.94 (2 H, m), 2.96 (1 H, dd, J = 9.3, 3.1 Hz), 3.40, 3.43 (2 H, ABq, J = 14.1 Hz) 6.73 (1 H, d, J = 1.1 Hz) 7.37 (1 H, dd, J = 5.7, 1.0 Hz), 8.28 (1 H, d, J = 5.7 Hz) |
| 17 | 2 | APCI/ESI+: 389.2 |
| 18 | 2 | ESI+: 403.4 |
| 19 | 2 | ESI+: 397.1 |
| 20 | 2 | ESI+: 381.2 |
| 21 | 2 | ESI+: 367.2 |
| 22 | 2 | ESI+: 365.1 |
| 23 | 3 | ESI+: 419.3 |

TABLE 8-continued

| Ex | Syn | DATA |
|---|---|---|
| 24 | 3 | ESI+: 407.2 |
| 25 | 3 | ESI+: 405.3 |
| 26 | 8 | ESI+: 367.2<br>¹H NMR (400 MHz, MeOH-d₄) δ ppm: 0.98 (3 H, t, J = 7.3 Hz) 1.40-1.51 (2 H, m) 1.72-1.81 (2 H, m) 2.02 (3 H, s) 2.46 (3 H, s) 2.53 (1 H, dd, J = 14.9, 11.6 Hz) 2.80-2.86 (2 H, m) 3.09-3.16 (2 H, m) 3.40 (2 H, s) 6.69-6.71 (1 H, m) 8.11 (1 H, d, J = 0.7 Hz) |
| 27 | 9 | ESI+: 365.2 |

TABLE 9

| PEx | Str |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |

TABLE 10

| PEx | Str |
|---|---|
| 9 | #1 (structure) |

TABLE 10-continued
| PEx | Str |
|---|---|
| 10 | * 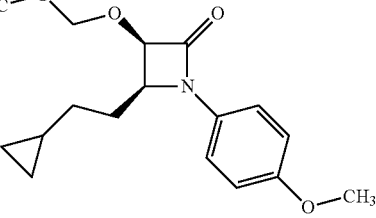 |
| 11 | * 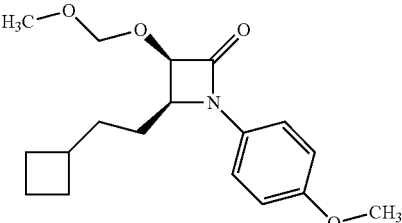 |
| 12 | #1 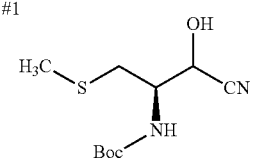 [SMILES: CSC[C@H](NC(=O)OC(C)(C)C)C(O)C#N] |
| 13 | #1 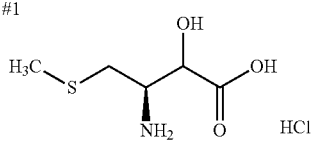 |
| 14 | #1 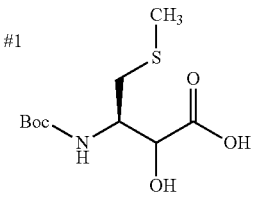 [SMILES: CSC[C@H](NC(=O)OC(C)(C)C)C(O)C(=O)O] |
| 15 | #1 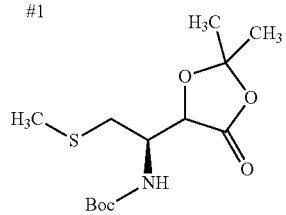 |
| 16 | * 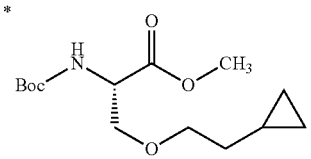 [SMILES: COC(=O)[C@H](COCCC1CC1)NC(=O)OC(C)(C)C] |
| 17 | * 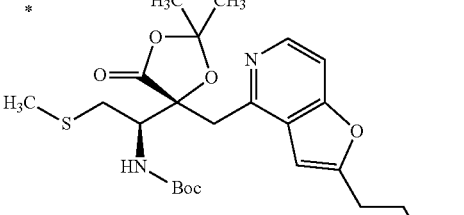 |
| 18 | * 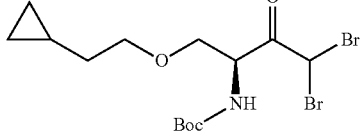 |
| 19 | #1 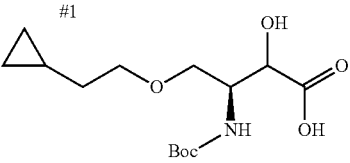 [SMILES: CC(C)(C)OC(=O)N[C@@H](COCCC1CC1)C(O)C(=O)O] |
| 20 | 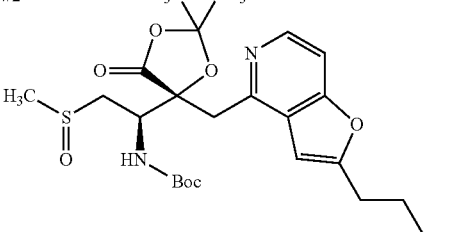 |
TABLE 11
| PEx | Str |
|---|---|
| 21 | #2 |

TABLE 11-continued
| PEx | Str |
|---|---|
| 22 | 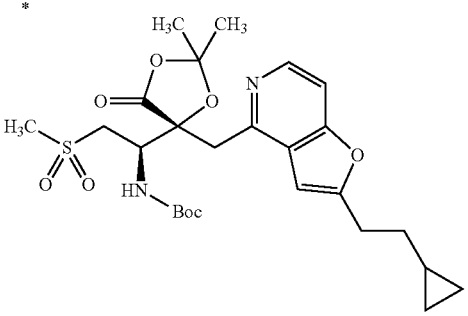 [SMILES: CC(C)(C)OC(=O)N[C@@H](CS(C)(=O)=O)[C@@]1(Cc2nccc3oc(CCC4CC4)cc23)OC(C)(C)OC1=O] |
| 23 | 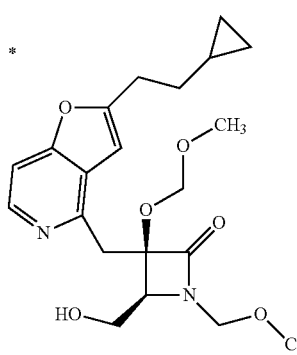 |
| 24 | 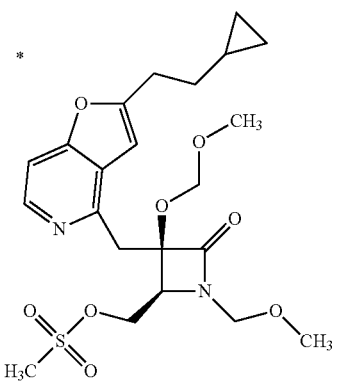 [SMILES: COCO[C@@]1(Cc2nccc3oc(CCC4CC4)cc23)C(=O)N(COC)[C@H]1COS(C)(=O)=O] |
| 25 | 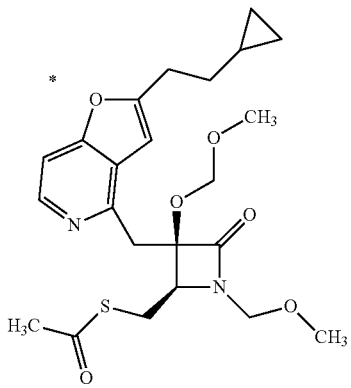 [SMILES: COCO[C@@]1(Cc2nccc3oc(CCC4CC4)cc23)C(=O)N(COC)[C@H]1CSC(C)=O] |
| 26 | 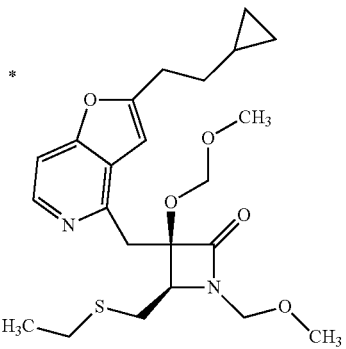 [SMILES: CCSC[C@@H]1N(COC)C(=O)[C@]1(Cc1nccc2oc(CCC3CC3)cc12)OCOC] |
| 27 | 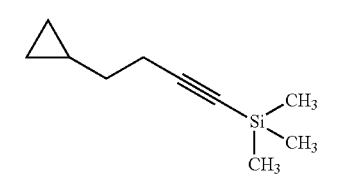 |
| 28 | 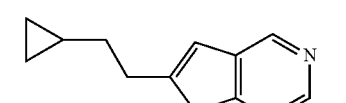 |
TABLE 12
| PEx | Str |
|---|---|
| 29 | 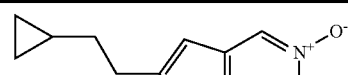 |
| 30 |  |
| 31 | 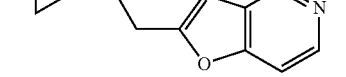 |
| 32 | 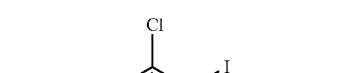 |
| 33 | 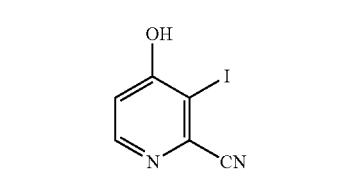 |

TABLE 12-continued
| PEx | Str |
|---|---|
| 34 | 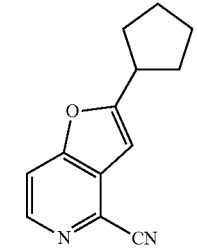 [SMILES: N#Cc1nccc2oc(C3CCCC3)cc12] |
| 35 | 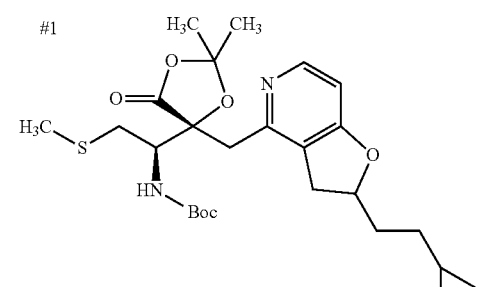 |
| 36 | 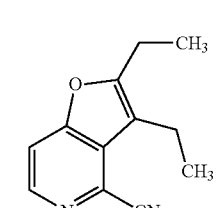 |
| 37 | 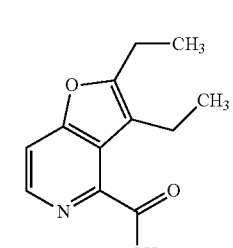 |
| 38 | 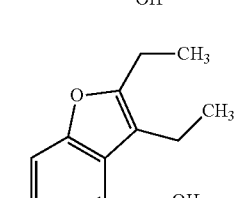 |
TABLE 13
| PEx | Str |
|---|---|
| 39 | 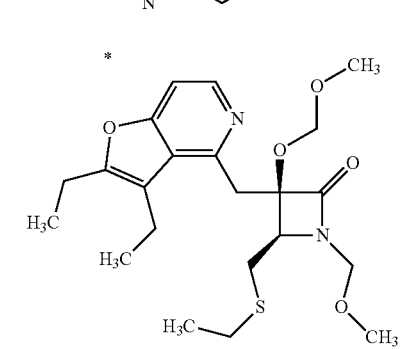 |
| 40 #1 | |
| 41 | |
| 42 | |
| 43 | |
| 44 * | |

TABLE 13-continued
| PEx | Str |
|---|---|
| 45 | 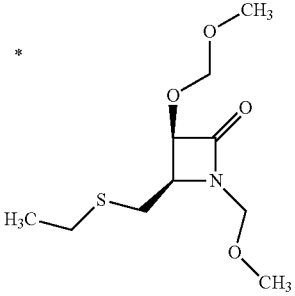 [SMILES: CCSC[C@H]1[C@@H](OCOC)C(=O)N1COC] |
| 46 | 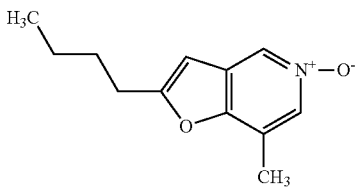 |
| 47 | 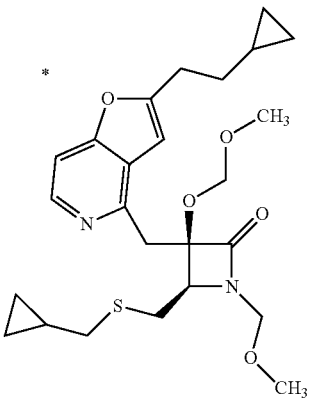 [SMILES: COCO[C@@]1(Cc2nccc3oc(CCC4CC4)cc23)C(=O)N(COC)[C@H]1CSCC1CC1] |
| 48 #1 | 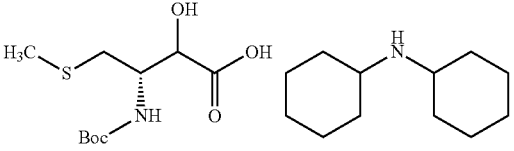 |
TABLE 14
| PEx | Str |
|---|---|
| 49 #1 | 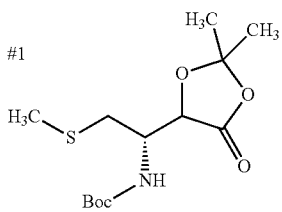 |
TABLE 14-continued
| PEx | Str |
|---|---|
| 50 | 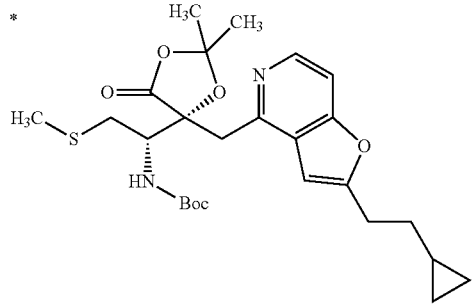 [SMILES: CSC[C@@H](NC(=O)OC(C)(C)C)[C@@]1(Cc2nccc3oc(CCC4CC4)cc23)OC(C)(C)OC1=O] |
| 51 | 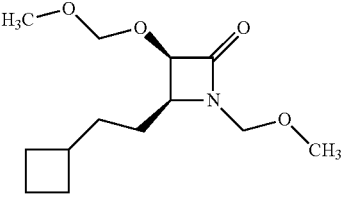 |
| 52 | 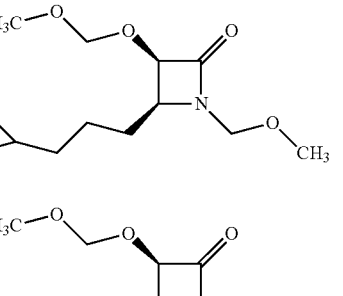 |
| 53 | 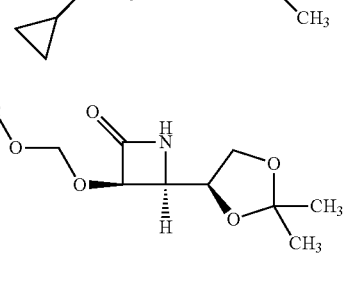 |
| 54 | 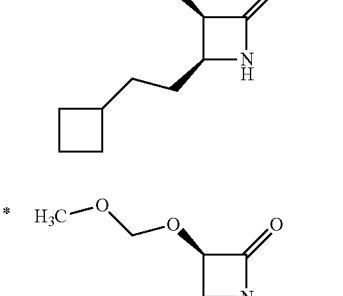 |
| 55 | 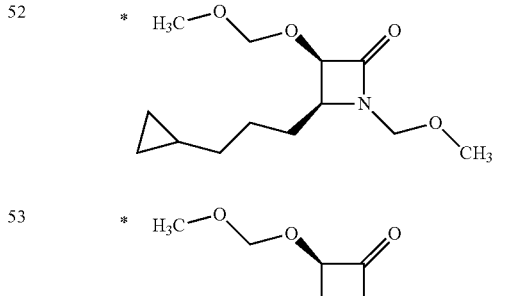 |
| 56 | 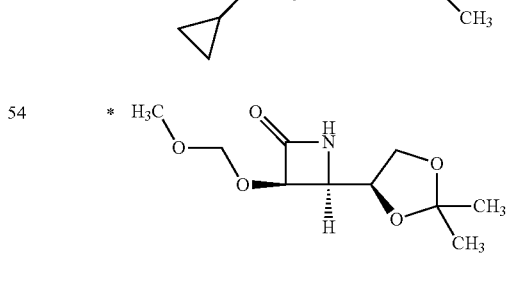 |

TABLE 14-continued
| PEx | Str |
|---|---|
| 57 | 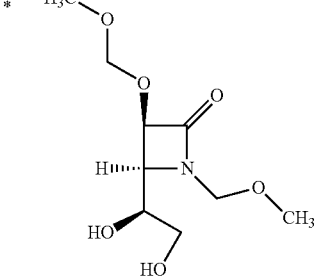 |
| 58 | 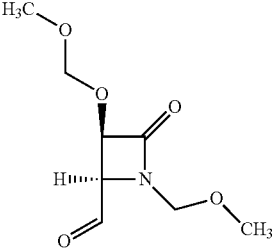 |
TABLE 15
| PEx | Str |
|---|---|
| 59 | 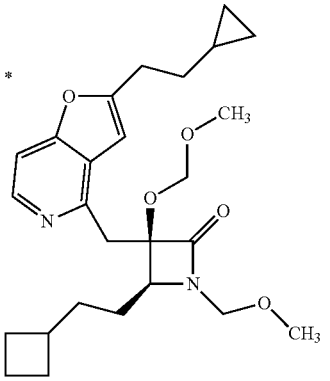 [SMILES: COCO[C@@]1(Cc2nccc3oc(CCC4CC4)cc23)C(=O)N(COC)[C@H]1CCC1CCC1] |
| 60 | 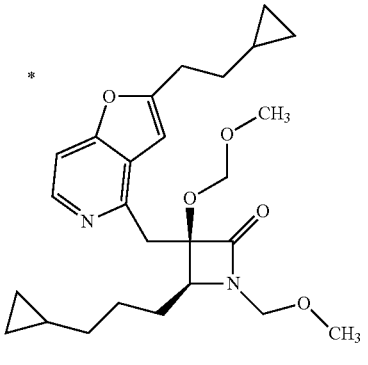 [SMILES: COCO[C@@]1(Cc2nccc3oc(CCC4CC4)cc23)C(=O)N(COC)[C@H]1CCCC1CC1] |
TABLE 15-continued
| PEx | Str |
|---|---|
| 61 | 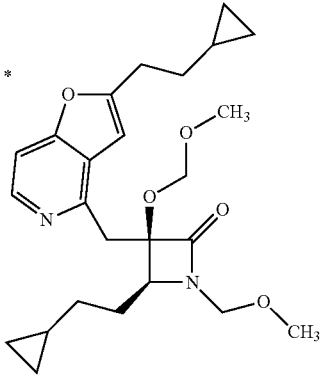 [SMILES: COCO[C@@]1(Cc2nccc3oc(CCC4CC4)cc23)C(=O)N(COC)[C@H]1CCC1CC1] |
| 62 | 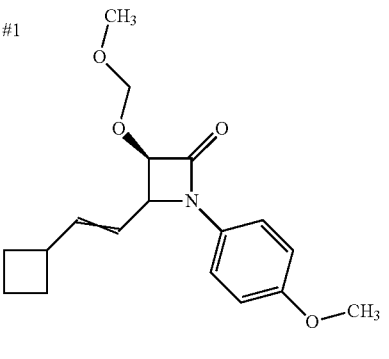 [SMILES: COCO[C@H]1C(=O)N(c2ccc(OC)cc2)C1C=CC1CCC1] |
| 63 | 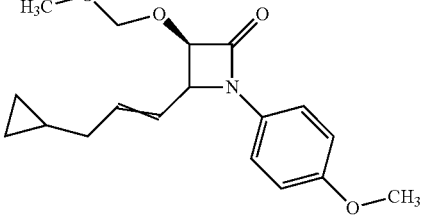 |
| 64 | 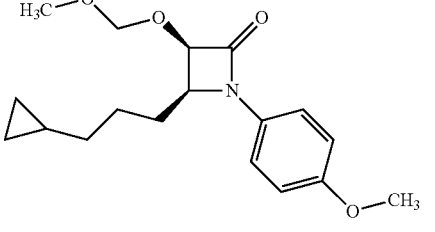 |
| 65 | 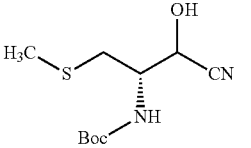 |
| 66 | 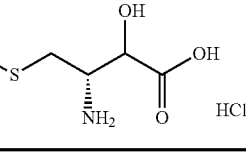 |

TABLE 16
| PEx | Str |
|---|---|
| 67 | #1 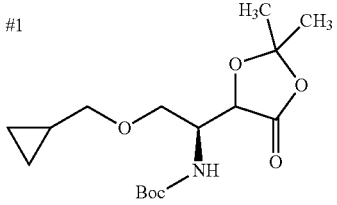 [SMILES: CC(C)(C)OC(=O)N[C@@H](COCC1CC1)C1OC(C)(C)OC1=O] |
| 68 | #1 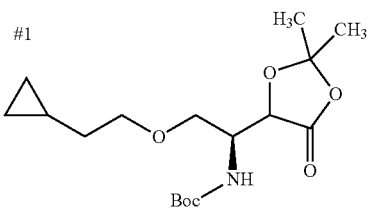 [SMILES: CC(C)(C)OC(=O)N[C@@H](COCCC1CC1)C1OC(C)(C)OC1=O] |
| 69 | * 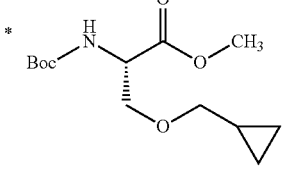 |
| 70 | * 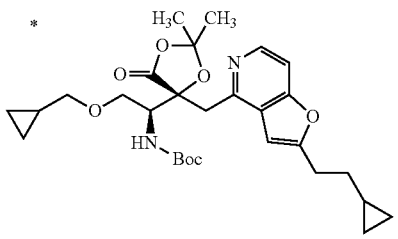 [SMILES: CC(C)(C)OC(=O)N[C@@H](COCC1CC1)[C@@]1(Cc2nccc3oc(CCC4CC4)cc23)OC(C)(C)OC1=O] |
| 71 | * 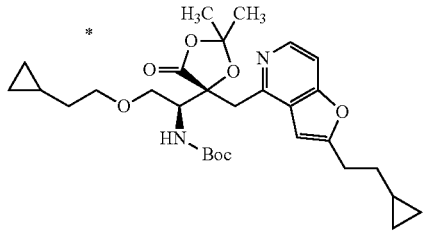 [SMILES: CC(C)(C)OC(=O)N[C@@H](COCCC1CC1)[C@@]1(Cc2nccc3oc(CCC4CC4)cc23)OC(C)(C)OC1=O] |
| 72 | * 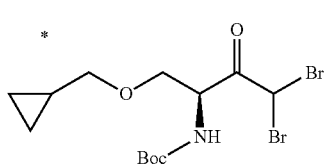 [SMILES: CC(C)(C)OC(=O)N[C@@H](COCC1CC1)C(=O)C(Br)Br] |
TABLE 16-continued
| PEx | Str |
|---|---|
| 73 | #1 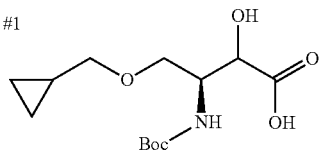 [SMILES: CC(C)(C)OC(=O)N[C@@H](COCC1CC1)C(O)C(=O)O] |
| 74 | * 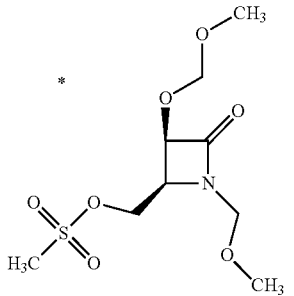 |
| 75 | * 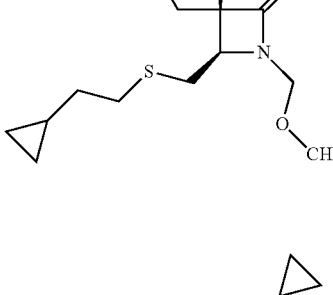 |
| 76 | * 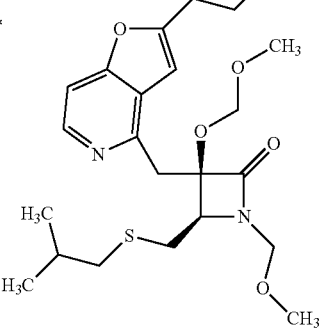 |

TABLE 17
| PEx | Str |
|---|---|
| 77 | 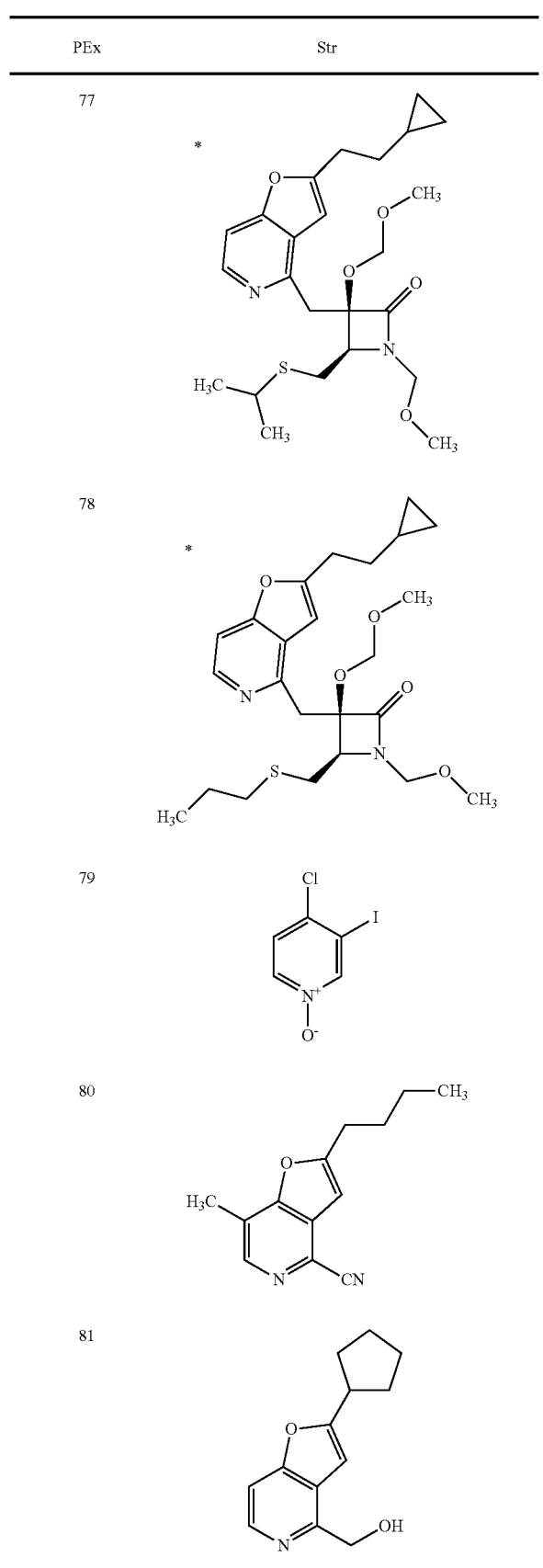 |
| 78 | |
| 79 | |
| 80 | |
| 81 | |
TABLE 17-continued
| PEx | Str |
|---|---|
| 82 | 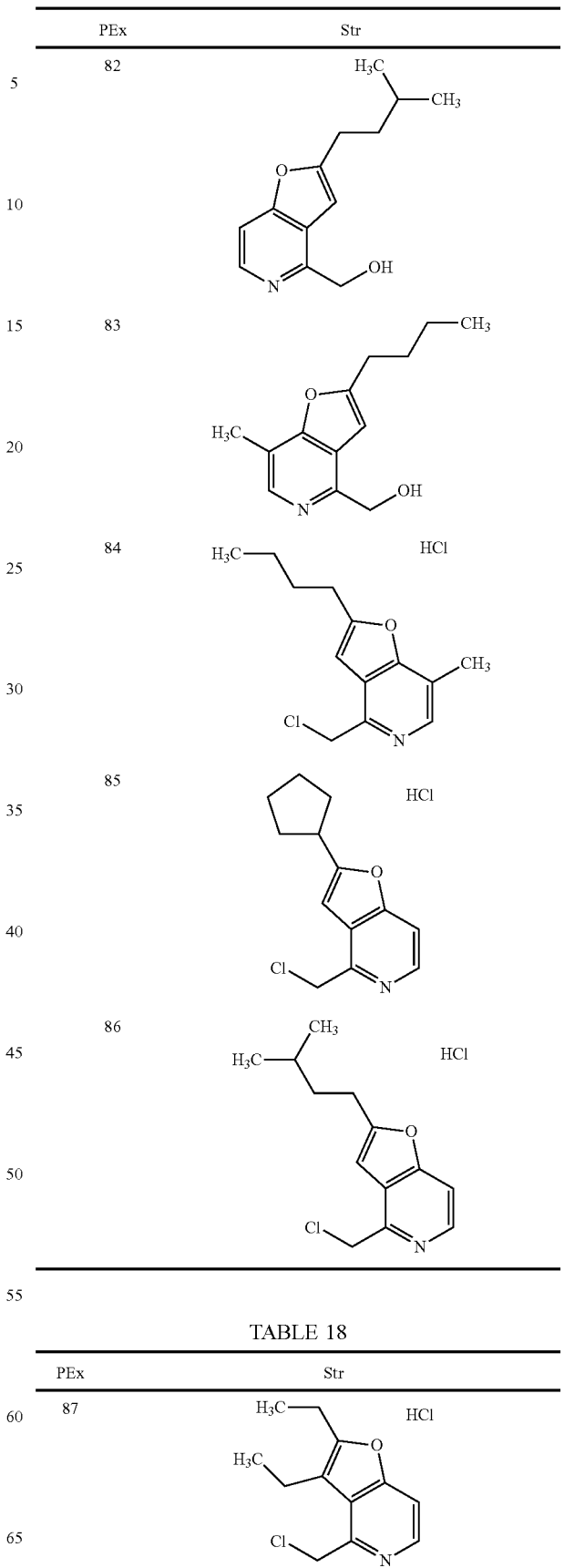 |
| 83 | |
| 84 | |
| 85 | |
| 86 | |
TABLE 18
| PEx | Str |
|---|---|
| 87 | |

TABLE 18-continued
| PEx | Str |
|---|---|
| 88 | 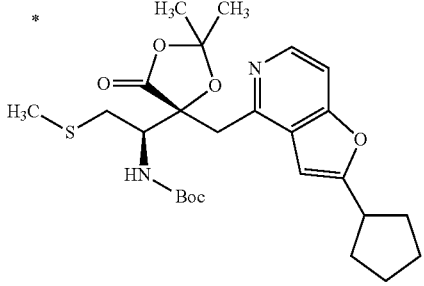 [SMILES: CSC[C@H](NC(=O)OC(C)(C)C)[C@@]1(Cc2nccc3oc(C4CCCC4)cc23)OC(C)(C)OC1=O] |
| 89 | 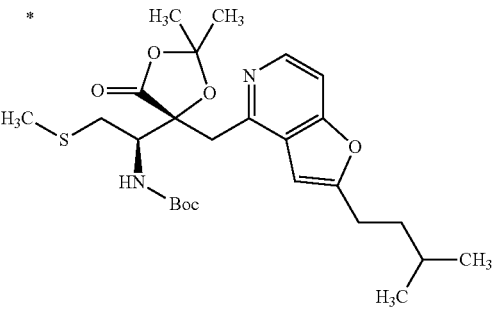 [SMILES: CSC[C@H](NC(=O)OC(C)(C)C)[C@@]1(Cc2nccc3oc(CCC(C)C)cc23)OC(C)(C)OC1=O] |
| 90 | 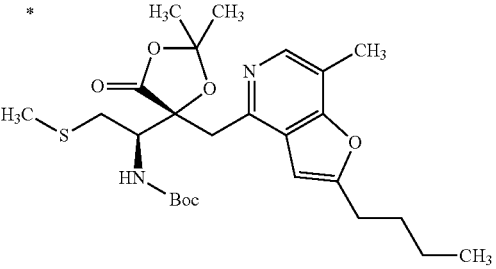 [SMILES: CCCCc1cc2c(C[C@]3([C@H](CSC)NC(=O)OC(C)(C)C)OC(C)(C)OC3=O)ncc(C)c2o1] |
| 91 | 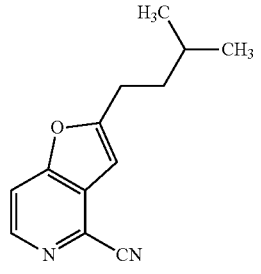 [SMILES: CC(C)CCc1cc2c(C#N)nccc2o1] |
| 92 | 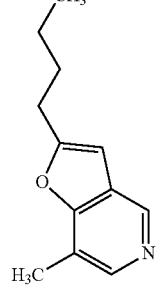 |
| 93 | 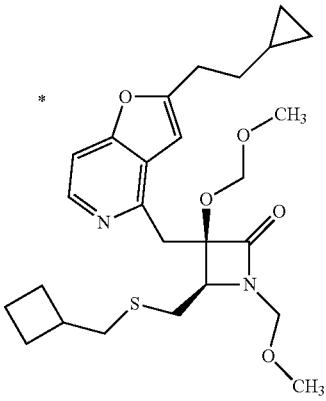 [SMILES: COCO[C@@]1(Cc2nccc3oc(CCC4CC4)cc23)C(=O)N(COC)[C@H]1CSCC1CCC1] |
| 94 | 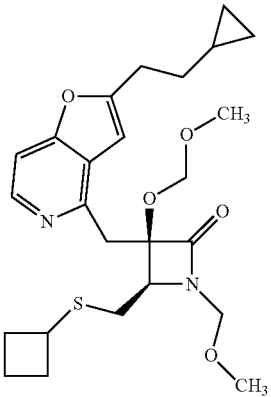 |
TABLE 19
| PEx | PSyn | DATA |
|---|---|---|
| 1 | — | ESI+: 338.2 |
| 2 | — | ESI+: 200.1 |
| 3 | — | ESI+: 298.2 [M + Na]+ |
| 4 | — | ESI+: 298.2 |
| 5 | — | CI+: 266.1 |
| 6 | — | ESI+: 206.1 |
| 7 | — | ESI+: 384.3 [M + Na]+ |
| 8 | — | ESI+: 561.3 |
| 9 | — | ESI+: 304.1 |
| 10 | — | ESI+: 306.2 |
| 11 | — | ESI+: 320.3 |
| 12 | — | ESI+: 269.0 [M + Na]+ |
| 13 | — | ESI+: 165.9 |
| 14 | — | ESI+: 288.1 [M + Na]+ |
| 15 | — | ESI+: 328.1 [M + Na]+ |
| 16 | — | ESI+: 288.1 |
| 17 | — | ESI+: 505.4 |
| 18 | — | ESI+: 450.0, 451.9, 454.0 [M + Na]+ |
| 19 | — | ESI−: 302.1 |
| 20 | — | ESI+: 250.2 |
| 21 | — | ESI+: 521.2 |
| 22 | — | ESI+: 537.3 |
| 23 | — | ESI+: 405.1 |
| 24 | — | ESI+: 483.1 |
| 25 | — | ESI+: 463.2 |
| 26 | — | ESI+: 449.3 |
| 27 | — | CI+: 167.2 |
| 28 | — | ESI+: 188.1 |
| 29 | — | ESI+: 204.0 |
| 30 | — | ESI+: 213.1 |

TABLE 20

| PEx | PSyn | DATA |
|---|---|---|
| 31 | — | ESI+: 218.1 |
| 32 | — | ESI+: 265.0, 267.0 |
| 33 | — | ESI+: 247.0 |
| 34 | — | ESI+: 447.3 |
| 35 | — | ESI+: 401.4 |
| 36 | — | ESI+: 222.1 |
| 37 | — | ESI+: 240.1, 242.1 |
| 38 | — | ESI+: 509.2 |
| 39 | — | ESI+: 213.1 |
| 40 | — | ESI+: 507.3 |
| 41 | — | ESI+: 201.0 |
| 42 | — | ESI+: 220.1 |
| 43 | — | ESI+: 206.1 |
| 44 | — | ESI+: 437.4 |
| 45 | — | ESI+: 272.1 [M + Na]+ |
| 46 | — | ESI+: 206.1 |
| 47 | — | ESI+: 475.2 |
| 48 | — | ESI+: 288.1 [M + Na]+ |
| 49 | — | ESI+: 328.1 [M + Na]+ |
| 50 | — | ESI+: 505.3 |
| 51 | 1 | ESI+: 258.1 |
| 52 | 1 | ESI+: 258.2 |
| 53 | 1 | ESI+: 244.2 |
| 54 | 2 | ESI+: 232.2 |
| 55 | 2 | ESI+: 214.1 |
| 56 | 2 | ESI+: 214.1 |
| 57 | 4 | ESI+: 236.0 |
| 58 | 5 | ESI+: 204.1 |
| 59 | 8 | ESI+: 457.4 |
| 60 | 8 | ESI+: 457.4 |

TABLE 21

| PEx | PSyn | DATA |
|---|---|---|
| 61 | 8 | ESI+: 443.3 |
| 62 | 9 | ESI+: 318.2 |
| 63 | 9 | ESI+: 318.2 |
| 64 | 10 | ESI+: 320.2 |
| 65 | 12 | ESI+: 269.1 [M + Na]+ |
| 66 | 13 | ESI+: 166.0 |
| 67 | 15 | ESI+: 330.1 |
| 68 | 15 | ESI+: 366.2 [M + Na]+ |
| 69 | 16 | ESI+: 296.2 [M + Na]+ |
| 70 | 17 | ESI+: 529.5 |
| 71 | 17 | ESI+: 543.3 |
| 72 | 18 | ESI+: 436.0, 438.0, 440.0 [M + Na]+ |
| 73 | 19 | ESI+: 290.1 |
| 74 | 24 | ESI+: 306.0 [M + Na]+ |
| 75 | 26 | ESI+: 489.2 |
| 76 | 26 | ESI+: 477.2 |
| 77 | 26 | ESI+: 463.2 |
| 78 | 26 | ESI+: 463.2 |
| 79 | 29 | ESI+: 255.9, 257.9 |
| 80 | 30 | ESI+: 215.0 |
| 81 | 31 | ESI+: 218.1 |
| 82 | 31 | ESI+: 220.2 |
| 83 | 31 | ESI+: 220.2 |
| 84 | 37 | APCI/ESI+: 238.1 |
| 85 | 37 | ESI+: 236.1, 238.1 |
| 86 | 37 | ESI+: 238.1, 240.1 |
| 87 | 37 | ESI+: 224.1, 226.1 |
| 88 | 38 | ESI+: 505.4 |
| 89 | 38 | ESI+: 507.5 |
| 90 | 38 | ESI+: 507.4 |
| 91 | 39 | ESI+: 215.1 |
| 92 | 39 | ESI+: 190.1 |
| 93 | 47 | ESI+: 489.2 |
| 94 | 47 | ESI+: 475.2 |

INDUSTRIAL APPLICABILITY

The compound represented by Formula (I) or a salt thereof has inhibitory activity against P-LAP, i.e. the AVP-degrading enzyme, and maintains and/or increases an endogenous AVP level to reduce urine production. Such a compound thus is expected to be used as an agent for treating nocturia, and is also expected to be used as an agent for treating any other voiding dysfunction or polyuria associated with a decreased AVP level, such as pollakiuria, urinary incontinence, and nocturnal enuresis.

The invention claimed is:

1. A compound represented by Formula (I) or a salt thereof:

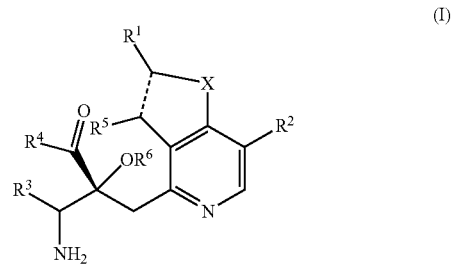

wherein:
X is O or S;
a dotted line is a single bond or a double bond;
$R^1$ is lower alkyl which optionally has one to four substituents selected from the Group $G^1$, cycloalkyl which optionally has one to five substituents selected from the Group $G^2$, or -lower alkylene-(cycloalkyl which optionally has one to five substituents selected from the Group $G^2$);
$R^2$ and $R^5$ are the same or different from each other, and are H, lower alkyl or cycloalkyl;
$R^3$ is -lower alkylene-$X^3$-lower alkyl, -lower alkylene-$X^3$-lower alkylene-(cycloalkyl which optionally has one to five substituents selected from the Group $G^2$), -lower alkylene-(cycloalkyl which optionally has one to five substituents selected from the Group $G^2$), or -lower alkylene-$X^3$-(cycloalkyl which optionally has one to five substituents selected from the Group $G^2$);
$X^3$ is O or $S(O)_n$, wherein n is 0, 1, or 2;
$R^4$ is OH, $NH_2$, or —O-lower alkyl and $R^6$ is H; or $R^4$ and $R^6$ are linked to each other to form, together with —C(=O)—C—O— to which they are attached, 2,2-di(lower alkyl)-4-oxo-1,3-dioxolane-5,5-diyl;
the Group $G^1$ consists of halogen, OH, —O-lower alkyl, —S-lower alkyl, and —O-(lower halogenoalkyl); and
the Group $G^2$ consists of lower alkyl, halogen, lower halogenoalkyl, OH, —O-lower alkyl, —S-lower alkyl, and —O-lower halogenoalkyl.

2. The compound or a salt thereof according to claim 1, wherein $R^4$ is OH, $NH_2$, or —O-lower alkyl and $R^6$ is H.

3. The compound or a salt thereof according to claim 2, wherein X is O, and a dotted line is a single bond or a double bond; or X is S, and a dotted line is a double bond.

4. The compound or a salt thereof according to claim 3, wherein:
$R^1$ is lower alkyl which optionally has one to four substituents selected from the group consisting of halogen, OH, and —O-lower alkyl; cycloalkyl which is optionally substituted by one to two lower alkyls; or -lower alkylene-(cycloalkyl which is optionally substituted by one to two lower alkyls);
$R^3$ is -lower alkylene-$X^3$-lower alkyl, -lower alkylene-$X^3$-lower alkylene-(cycloalkyl which is optionally substituted by one to two lower alkyls), -lower alkylene-(cycloalkyl which is optionally substituted by one to two lower alkyls), or -lower alkylene-$X^3$-(cycloalkyl which is optionally substituted by one to two lower alkyls); and $R^2$ and $R^5$ are the same or different from each other, and are H or lower alkyl.

5. The compound or a salt thereof according to claim 4, wherein:

$R^1$ is lower alkyl which optionally has one to four substituents selected from the group consisting of halogen and OH; cycloalkyl; or -lower alkylene-cycloalkyl; and $R^3$ is -lower alkylene-S(O)$_n$-lower alkyl, -lower alkylene-O-lower alkylene-cycloalkyl, -lower alkylene-S-lower alkylene-cycloalkyl, -lower alkylene-cycloalkyl, or -lower alkylene-S-cycloalkyl.

6. The compound or a salt thereof according to claim 5, wherein $R^1$ is lower alkyl, cycloalkyl, or -lower alkylene-cycloalkyl; $R^3$ is -lower alkylene-S-lower alkyl, -lower alkylene-O-lower alkylene-cycloalkyl, -lower alkylene-S-lower alkylene-cycloalkyl, -lower alkylene-cycloalkyl, or -lower alkylene-S-cycloalkyl; $R^2$ is H or lower alkyl; $R^5$ is H; and $R^4$ is OH.

7. The compound or a salt thereof according to claim 6, wherein X is O, and a dotted line is a double bond; $R^1$ is lower alkyl, or -lower alkylene-cycloalkyl; and $R^3$ is -lower alkylene-S-lower alkyl, or -lower alkylene-cycloalkyl.

8. The compound or a salt thereof according to claim 2, wherein X is O, and a dotted line is a double bond.

9. The compound or a salt thereof according to claim 1, which is a compound selected from the group consisting of the following compounds, or a salt thereof:

(2R,3R)-3-amino-2-{[2-(2-cyclopropylethyl)furo[3,2-c]pyridin-4-yl]methyl}-4-(ethylsulfanyl)-2-hydroxybutanoic acid, (2R,3S)-3-amino-5-cyclopropyl-2-{[2-(2-cyclopropylethyl)furo[3,2-c]pyridin-4-yl]methyl}-2-hydroxypentanoic acid, (2R,3R)-3-amino-2-{[2-(2-cyclopropylethyl)furo[3,2-c]pyridin-4-yl]methyl}-2-hydroxy-4-(methylsulfanyl)butanoic acid, and (2R,3R)-3-amino-2-[(2-butyl-7-methylfuro[3,2-c]pyridin-4-yl)methyl]-2-hydroxy-4-(methylsulfanyl)butanoic acid.

10. A pharmaceutical composition comprising the compound or a salt thereof according to claim 1.

11. The pharmaceutical composition according to claim 10, which is an agent for treating nocturia.

12. A pharmaceutical composition comprising the compound or a salt thereof according to claim 1 and an excipient.

13. A method of treating nocturia comprising administering an effective amount of the compound or a salt thereof according to claim 1 to a subject.

14. The compound or a salt thereof according to claim 9, which is (2R,3R)-3-amino-2-{[2-(2-cyclopropylethyl)furo[3,2-c]pyridin-4-yl]methyl}-4-(ethylsulfanyl)-2-hydroxybutanoic acid or a salt thereof.

15. The compound or a salt thereof according to claim 9, which is (2R,3S)-3-amino-5-cyclopropyl-2-{[2-(2-cyclopropylethyl)furo[3,2-c]pyridin-4-yl]methyl}-2-hydroxypentanoic acid or a salt thereof.

16. The compound or a salt thereof according to claim 9, which is (2R,3R)-3-amino-2-{[2-(2-cyclopropylethyl)furo[3,2-c]pyridin-4-yl]methyl}-2-hydroxy-4-(methylsulfanyl)butanoic acid or a salt thereof.

17. The compound or a salt thereof according to claim 9, which is (2R,3R)-3-amino-2-[(2-butyl-7-methylfuro[3,2-c]pyridin-4-yl)methyl]-2-hydroxy-4-(methylsulfanyl)butanoic acid or a salt thereof.

* * * * *